(12) United States Patent
Ko et al.

US010688197B2

(10) Patent No.: US 10,688,197 B2
(45) Date of Patent: Jun. 23, 2020

(54) NON-ALCOHOLIC FATTY LIVER REGULATOR 14-3-3 PROTEIN

(71) Applicant: Korea University Research and Business Foundation, Seoul (KR)

(72) Inventors: Jesang Ko, Seoul (KR); Sodam Park, Jeonju-si (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 16/445,120

(22) Filed: Jun. 18, 2019

(65) Prior Publication Data

US 2019/0307902 A1 Oct. 10, 2019

Related U.S. Application Data

(62) Division of application No. 15/747,320, filed as application No. PCT/KR2016/008131 on Jul. 26, 2016, now Pat. No. 10,363,322.

(30) Foreign Application Priority Data

Jul. 31, 2015 (KR) ........................ 10-2015-0108944

(51) Int. Cl.
| | |
|---|---|
| *A61K 48/00* | (2006.01) |
| *C07H 21/04* | (2006.01) |
| *A61K 31/713* | (2006.01) |
| *C12Q 1/6883* | (2018.01) |
| *G01N 33/50* | (2006.01) |
| *G01N 33/68* | (2006.01) |
| *A61K 39/395* | (2006.01) |
| *A61P 1/16* | (2006.01) |
| *G01N 33/53* | (2006.01) |

(52) U.S. Cl.
CPC ........ *A61K 48/0066* (2013.01); *A61K 31/713* (2013.01); *A61K 39/395* (2013.01); *A61K 48/00* (2013.01); *A61P 1/16* (2018.01); *C12Q 1/6883* (2013.01); *G01N 33/5041* (2013.01); *G01N 33/5067* (2013.01); *G01N 33/5308* (2013.01); *G01N 33/6872* (2013.01); *C12Q 2600/158* (2013.01); *G01N 2333/4703* (2013.01); *G01N 2800/085* (2013.01)

(58) Field of Classification Search
CPC ............................. A61K 31/713; C12N 15/113
See application file for complete search history.

(56) References Cited

PUBLICATIONS

International Search Report for PCT/KR2016/008131, dated Oct. 20, 2016.
Yunhee Hwang, "Roles of 14-3-3β and ? in regulation of the glucocorticoid receptor transcriptional activation and hepatic gluconeogenesis", Master's Thesis, Korea University Graduate School, Department of Biotechnology, Feb. 2013.
Sodam Park et al., "14-3-3β and ? differentially regulate peroxisome proliferator activated receptor ?2 transactivation and hepatic lipid metabolism", Biochimica et Biophysica Acta(BBA)—Gene Regulatory Mechanisms, Oct. 2015, pp. 1237-1247, vol. 1849, No. 10.
Yi Yang et al., "Alpha-lipoic acid attenuates insulin resistance and improves glucose metabolism in high fat diet-fed mice", Acta Pharmacologica Sinica, 2014, pp. 1285-1292, vol. 35, No. 10.
Qiang Ge et al., "Structural Characterization of a Unique Interface between Carbohydrate Response Element-binding Protein (ChREBP) and 14-3-3β Protein", Journal of Biological Chemistry, Dec. 7, 2012, pp. 41914-41921, vol. 287, No. 50.
Atsushi Kosaki et al., "14-3-3βProtein Associates with Insulin Receptor Substrate 1 and Decreases Insulin-stimulated Phosphatidylinositol 3'-Kinase Activity in 3T3L1 Adipocytes", Journal of Biological Chemistry, Jan. 9, 1998, pp. 940-944, vol. 273, No. 2.

*Primary Examiner* — Amy H Bowman
(74) *Attorney, Agent, or Firm* — Sughrue Mion, PLLC

(57) ABSTRACT

The present invention relates to the 14-3-3 protein which is a non-alcoholic fatty liver regulating factor. According to the present invention, two isoform proteins of 14-3-3, i.e., 14-3-3β and 14-3-3γ, are different regulating factors for regulating the transcriptional activity of $PPAR\gamma_2$. 14-3-3β increases the transcriptional activity of $PPAR\gamma_2$ by binding to $PPAR\gamma_2$, on the other hand, 14-3-3γ plays a role in decreasing the transcriptional activity of $PPAR\gamma_2$. Thus, 14-3-3β and 14-3-3γ, which are $PPAR\gamma_2$ regulating factors, are proteins that play a vital role in lipid metabolism, and may be used as a target for the prevention or treatment of fatty liver.

2 Claims, 14 Drawing Sheets

Specification includes a Sequence Listing.

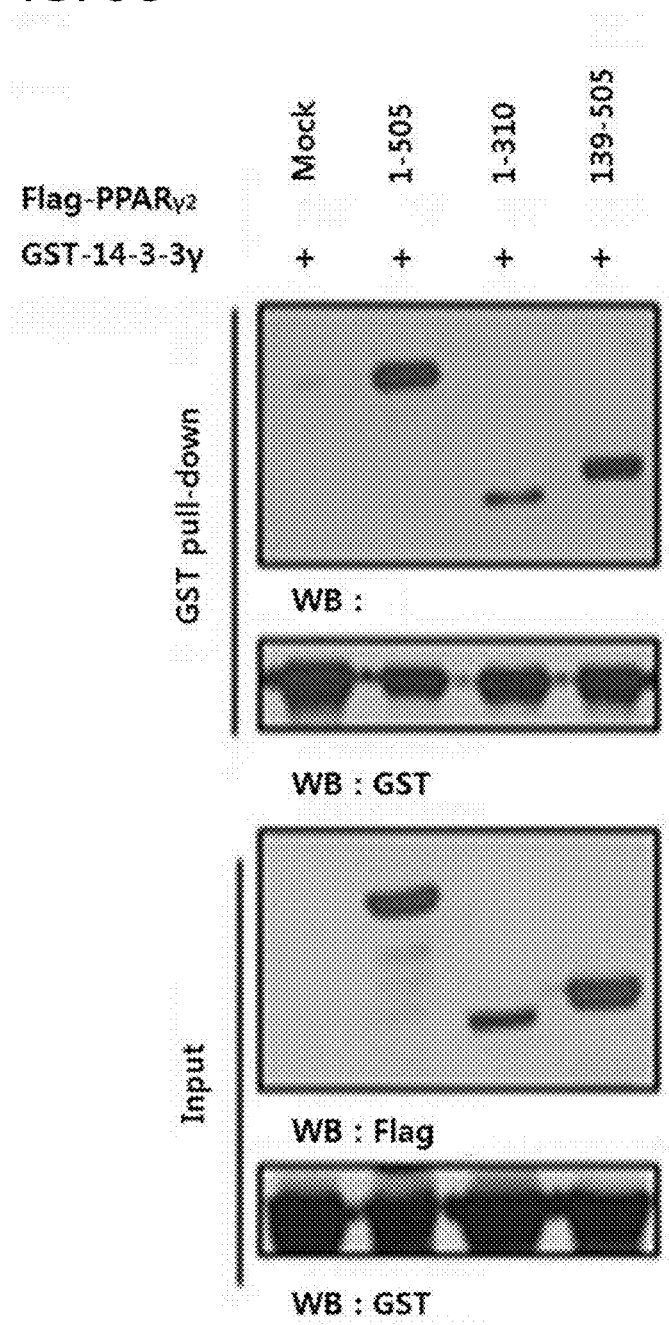

NON-ALCOHOLIC FATTY LIVER REGULATOR 14-3-3 PROTEIN

CROSS-REFERENCE TO RELATED APPLICATIONS

This application is a Rule 53(b) Divisional application of U.S. application Ser. No. 15/747,320 filed Jan. 24, 2018, which is a National Stage of International Application No. PCT/KR2016/008131 filed Jul. 26, 2016, claiming priority based on Korean Patent Application No. 10-2015-0108944 filed Jul. 31, 2015, the contents of all of which are incorporated herein by reference in their entirety.

TECHNICAL FIELD

The present invention relates to a non-alcoholic fatty liver regulating factor 14-3-3 protein.

BACKGROUND ART

Non-alcoholic fatty liver disease (NAFLD) is a representative liver disease that causes liver inflammation and damage. When aggravated, NAFLD develops into non-alcoholic steatohepatitis (NAS) with symptoms such as cirrhosis and fibrosis. According to recent reports, it has been known that peroxisome proliferator activated receptor (PPAR)$\gamma_2$ as a transcriptional factor is overexpressed and activated in the liver of fatty liver patients. In addition, the activation of PPAR$\gamma_2$ induces the expression of a variety of target proteins involved in lipid metabolism of the liver. Proteins, so-called 14-3-3, involved in the activity of such a transcriptional factor exist as seven isoforms ($\alpha/\beta$, $\varepsilon$, $\eta$, $\gamma$, $\tau/\theta$, $\delta/\zeta$, and $\sigma$). 14-3-3 proteins are known to bind to the phosphorylation site of a transcriptional factor and regulate the activity of the transcriptional factor, and are also involved in regulating metabolism-associated transcriptional factors. Thus, the inventors of the present invention investigated the role of 14-3-3 proteins in the onset and regulation of fatty liver and, as a result, verified that 14-3-3$\beta$ and 14-3-3$\gamma$, which are regulating factors, are proteins that play a vital role in lipid metabolism, and can be used as a target for the treatment of non-alcoholic fatty liver, thus completing the present invention.

SUMMARY OF THE INVENTION

Technical Problem

The present invention provides a use of 14-3-3$\beta$ and 14-3-3$\gamma$ for the prevention of non-alcoholic fatty liver or the development of a therapeutic drug.

However, technical problems to be achieved by the present invention are not limited to the aforementioned technical problem, and other unmentioned technical problems will become apparent to those skilled in the art from the following description.

Technical Solution

To achieve the above object, the present invention provides a pharmaceutical composition for the prevention or treatment of non-alcoholic fatty liver which includes an inhibitor against the 14-3-3$\beta$ gene, wherein the inhibitor includes an antisense oligonucleotide, siRNA, shRNA or miRNA against the 14-3-3$\beta$ gene, or a vector including the same.

The present invention also provides a pharmaceutical composition for the prevention or treatment of non-alcoholic fatty liver which includes the 14-3-3$\gamma$ gene or 14-3-3$\gamma$ protein.

The present invention also provides a composition for diagnosing non-alcoholic fatty liver, the composition including a probe for measuring a level of mRNA or a protein of the 14-3-3$\beta$ gene and/or the 14-3-3$\gamma$ gene from a sample of a patient suspected of having fatty liver.

The present invention also provides a method of screening a drug for the prevention or treatment of non-alcoholic fatty liver, the method including: bringing a cell including the 14-3-3$\beta$ gene or 14-3-3$\beta$ protein or the 14-3-3$\gamma$ gene or 14-3-3$\gamma$ protein into contact with a candidate material in vitro; and measuring a change in the expression amount of the gene or the protein by the candidate material.

The present invention also provides a method of screening a drug for the prevention or treatment of non-alcoholic fatty liver, the method including: bringing the 14-3-3$\beta$ protein and/or the 14-3-3$\gamma$ protein into contact with a candidate material together with the PPAR$\gamma_2$ protein; and measuring a change in binding of the 14-3-3$\beta$ protein and/or the 14-3-3$\gamma$ protein to the PPAR$\gamma_2$ protein by the candidate material.

Advantageous Effects

According to the present invention, 14-3-3$\beta$ and 14-3-3$\gamma$, which are two isoform proteins of 14-3-3, are different regulating factors that regulate the transcriptional activity of PPAR$\gamma_2$. 14-3-3$\beta$ increases the transcriptional activity of PPAR$\gamma_2$ by binding to PPAR$\gamma_2$, on the other hand, 14-3-3$\gamma$ plays a role in decreasing the transcriptional activity of PPAR$\gamma_2$. Thus, 14-3-3$\beta$ and 14-3-3$\gamma$ as regulating factors of PPAR$\gamma_2$ are proteins that play a vital role in lipid metabolism, and may be used as a target for the prevention or treatment of non-alcoholic fatty liver.

BRIEF DESCRIPTION OF DRAWINGS

FIGS. 2A and 2B illustrate results of verifying binding with PPAR$\gamma_2$ according to treatment of pioglitazone, which is a PPAR$\gamma_2$ ligand, wherein FIG. 2A illustrates verification results of binding between PPAR$\gamma_2$ and 14-3-3$\beta$, and FIG. 2B illustrates verification results of binding between PPAR$\gamma_2$ and 14-3-3$\gamma$.

FIG. 3C illustrates verification results of deletion mutation of PPARγ$_2$ and binding between the deletion mutants and 14-3-3γ by GST-pull down assay.

FIGS. 5A and 5B illustrate verification results of binding with PPARγ$_2$ according to overexpression of 14-3-3γ or 14-3-3β, wherein FIG. 5A illustrates verification results of binding between 14-3-3β and PPARγ$_2$ according to overexpression of 14-3-3γ, and FIG. 5B illustrates verification results of binding between 14-3-3γ and PPARγ$_2$ according to overexpression of 14-3-3β.

FIGS. 8A, 8B and 8C illustrate verification results of binding with PPARγ$_2$ according to oleic acid treatment and whether a PAR-RXR complex was formed according to overexpression of 14-3-3β and 14-3-3γ, wherein FIG. 8A illustrates verification results of binding between PPARγ$_2$ and 14-3-3β according to oleic acid treatment; FIG. 8B illustrates verification results of binding between PPARγ$_2$ and 14-3-3γ according to oleic acid treatment; and FIG. 8C illustrates results of verifying whether a PPAR-RXR complex was formed according to overexpression of 14-3-3β and 14-3-3γ.

FIGS. 9A, 9B and 9C illustrate verification results of changes in fat accumulation in primary mouse hepatocytes and HepG2 cells according to oleic acid treatment, overexpression of 14-3-3β and 14-3-3γ, or the inhibition of expression thereof, wherein FIG. 9A illustrates verification results of a change in fat accumulation according to oleic acid treatment; FIG. 9B illustrates verification results of a change in fat accumulation according to overexpression of 14-3-3β and 14-3-3γ; and FIG. 9C illustrates verification results of a change in fat accumulation according to the inhibition of 14-3-3β and 14-3-3γ expression.

FIGS. 10A and 10B illustrate verification results of changes in triglyceride accumulation in primary mouse hepatocytes and HepG2 cells according to overexpression of 14-3-3β and 14-3-3γ or the inhibition of expression thereof, wherein FIG. 10A illustrates verification results of a change in triglyceride accumulation according to overexpression of 14-3-3β and 14-3-3γ; and FIG. 10B illustrates verification results of a change in triglyceride accumulation according to the inhibition of 14-3-3β and 14-3-3γ expression.

DETAILED DESCRIPTION OF THE INVENTION

Figure 1A:
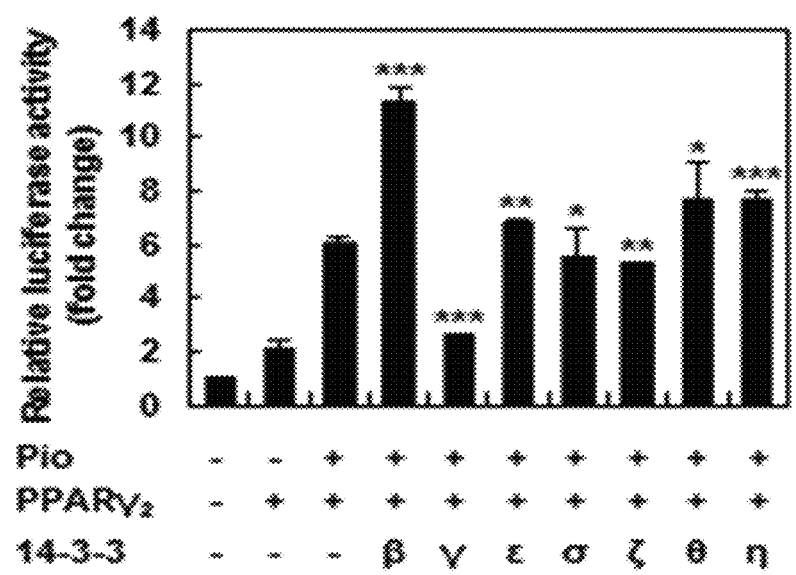
FIG. 1A illustrates results of verifying the transcriptional activity of PPAR$\gamma_2$ according to overexpression of 14-3-3 isoform proteins.

Hereinafter, constitutions of the present invention will be described in detail.

The inventors of the present invention discovered that 14-3-3β and 14-3-3γ, which are two isoform proteins, are different regulating factors that regulate the transcriptional activity of PPARγ$_2$. 14-3-3β increases the transcriptional activity of PPARγ$_2$ by binding to PPARγ$_2$, on the other hand, 14-3-3γ plays a role in decreasing the transcriptional activity of PPARγ$_2$. Since PPARγ$_2$ plays a vital role in NAFLD, 14-3-3β and 14-3-3γ were overexpressed in hepatocytes to investigate how 14-3-3β and 14-3-3γ affect fat accumulation. As a result, when 14-3-3β was overexpressed, the expression of target genes of PPARγ$_2$ involved in lipid metabolism increased and fat accumulation was enhanced, on the other hand, when 14-3-3γ was overexpressed, the expression of target genes of PPARγ$_2$ and fat accumulation were suppressed. That is, it was verified that 14-3-3β and 14-3-3γ as PPARγ$_2$ regulating factors are proteins that play a vital role in lipid metabolism, and may be used as a target protein for the treatment of NAFLD.

Therefore, the present invention provides a use of 14-3-3β and 14-3-3γ for preparing a pharmaceutical composition for the prevention or treatment of fatty liver.

More specifically, the present invention provides a pharmaceutical composition for the prevention or treatment of fatty liver which includes an inhibitor against the 14-3-3β gene, a use of the inhibitor against preparing a drug for the prevention or treatment of fatty liver, and a method of preventing or treating fatty liver, including administering the inhibitor to a subject.

In the present invention, 14-3-3β used as a target for regulating the transcriptional activity of PPARγ$_2$ involved in lipid metabolism refers to the 14-3-3β gene or is construed as referring to the 14-3-3β protein. Thus, an inhibitor against 14-3-3β is construed as including both an inhibitor against the 14-3-3β gene and an inhibitor against the 14-3-3β protein.

The 14-3-3β protein, the 14-3-3β gene, and the like are construed as including a variant or fragment thereof having substantially the same activity as the 14-3-3β protein, the 14-3-3β gene, or the like.

In one embodiment, the inhibitor against the 14-3-3β gene may be an inhibitor that inhibits expression of the gene to block PPARγ$_2$ binding by the inhibition of 14-3-3β protein expression. The 14-3-3β gene may be DNA encoding 14-3-3β or mRNA transcribed therefrom. Thus, the inhibitor against the 14-3-3β gene may be an inhibitor that interferes with transcription by binding to the gene itself or binds to the transcribed mRNA and thus interferes with translation of the mRNA.

In one embodiment, the inhibitor against the 14-3-3β gene may be an antisense oligonucleotide, siRNA, shRNA or miRNA against the 14-3-3β gene, or a vector including the same. Such antisense oligonucleotide, siRNA, shRNA or miRNA, or such a vector including the same may be constructed using a method known in the art. As used herein, the term "vector" refers to a gene construct including exogenous DNA inserted into a genome encoding polypeptides. The vector associated with the present invention is a vector in which a nucleic acid sequence inhibiting the gene is inserted into the genome, and the vector may be, for example, a DNA vector, a plasmid vector, a cosmid vector, a bacteriophage vector, a yeast vector, or a virus vector.

In one embodiment, the inhibitor against the 14-3-3β protein may be an inhibitor that blocks binding between the 14-3-3β protein and PPARγ$_2$ by binding to the 14-3-3β protein. For example, such an inhibitor may be a peptide or compound binding to the 14-3-3β protein, or the like. Such an inhibitor may be selected through a screening method described below such as protein structure analysis or the like, and may be designed using a method known in the art. In one embodiment, the inhibitor may be a polyclonal or monoclonal antibody against the 14-3-3β protein. Such a polyclonal or monoclonal antibody may be produced using an antibody production method known in the art.

When 14-3-3γ is overexpressed, the expression of target genes of PPARγ$_2$ and fat accumulation are suppressed, and thus the 14-3-3γ gene or the 14-3-3γ protein itself may be used as an active ingredient of a pharmaceutical composition for the prevention or treatment of non-alcoholic fatty liver.

Thus, the present invention provides a pharmaceutical composition for the prevention or treatment of non-alcoholic fatty liver which includes the 14-3-3γ gene.

The gene included as an active ingredient of a pharmaceutical composition may be included in the pharmaceutical composition in the form of the gene itself or a vector including the corresponding gene. The definition of the vector has already been provided above, and the type and construction method of such a vector are well known in the art.

The present invention also provides a pharmaceutical composition for the prevention or treatment of non-alcoholic fatty liver which includes the 14-3-3γ protein.

The pharmaceutical composition for the prevention or treatment of non-alcoholic fatty liver of the present invention may include natural or recombinant 14-3-3γ, or a 14-3-3γ protein having substantially the same biological activity as the natural or recombinant 14-3-3γ. The 14-3-3γ protein having substantially the same biological activity includes natural/recombinant 14-3-3γ, a functional equivalent thereto, and a functional derivative thereof.

The term "functional equivalent" as used herein refers to a variant having an amino acid sequence in which amino acids of the natural protein are partially or completely substituted, or are partially deleted or added, wherein the variant has substantially the same biological activity as that of natural 14-3-3γ.

The term "functional derivative" as used herein refers to a protein modified to increase or decrease physical or chemically properties of the 14-3-3γ protein, wherein the protein has substantially the same biological activity as that of natural 14-3-3γ.

The origin of the 14-3-3γ protein of the present invention is not particularly limited, but the 14-3-3γ protein may be preferably a protein derived from vertebrates, preferably, humans, mice, rats, or the like.

According to one embodiment, 14-3-3γ used in the present invention may be produced using a genetic engineering method known in the art from the known sequence.

When protein is produced using natural 14-3-3γ using a genetic engineering method, a protein produced using mammalian cells is considered to be more similar to natural 14-3-3γ than a protein produced using *Escherichia coli* (*E. coli*) or insect cells, in terms of activity or solubility of a protein.

The recombinant 14-3-3γ protein may be isolated using a general column chromatography method or the like. In addition, a protein purification degree may be identified by sodium dodecyl sulfate (SDS)-polyacrylamide gel electrophoresis (PAGE) or the like.

The pharmaceutical composition of the present invention may be prepared using a pharmaceutically suitable and biologically acceptable additive in addition to the active ingredient, and the additive may be a solubilizer such as an excipient, a disintegrant, a sweetener, a binder, a coating agent, a swelling agent, a lubricant, a glydents, a flavor enhancer, or the like.

The pharmaceutical composition of the present invention may be preferably formulated by including one or more pharmaceutically acceptable carriers in addition to the active ingredient, for the purpose of administering the pharmaceutical composition.

A pharmaceutically acceptable carrier for a composition formulated into a liquid solution may be suitable for sterilization and a body, and may be saline, sterile water, Ringer's solution, buffered saline, an albumin injection solution, a dextrose solution, a maltodextrin solution, glycerol, ethanol, or a mixture of two or more of these ingredients. When necessary, other general additives such as antioxidants, buffers, bacteriostatic agents, and the like may be added. In addition, the composition may be formulated into the form of injectable preparations such as aqueous solutions, suspensions, emulsions, or the like, pills, capsules, granules, or tablets by further adding a diluent, a dispersant, a surfactant, a binder, and a lubricant. Furthermore, the composition may be preferably formulated using an appropriate method known in the art according to diseases or ingredients using a method disclosed in Remington's Pharmaceutical Science, Mack Publishing Company, Easton Pa.

Pharmaceutical preparation forms of the pharmaceutical composition of the present invention may be granules, powder, coated tablets, tablets, capsules, suppositories, syrups, juices, suspensions, emulsions, drops, sustained release type preparations of an injectable liquid and an active compound, or the like.

The pharmaceutical composition of the present invention may be administered using a general method via an intravenous, intraarterial, intraperitoneal, intramuscular, intrasternal, percutaneous, intranasal, inhalation, topical, intrarectal, oral, intraocular, or intradermal route.

An effective amount of the active ingredient of the pharmaceutical composition of the present invention refers to an amount required to achieve an effect of preventing or treating diseases or an effect of inducing bone growth. Thus, the effective amount may be adjusted according to a variety of factors including type of diseases, the severity of diseases, types and amounts of an active ingredient and other ingredients included in the composition, type of formulation, ages, body weights, general health conditions, gender, and patient diet, administration time, administration route, excretion rate of the composition, treatment period, and simultaneously used drugs. For example, in the case of an adult, the inhibitor of the present invention may be administered once or several times a day at a dose of 0.1 ng/kg to 10 g/kg as a compound, at a dose of 0.1 ng/kg to 10 g/kg as a polypeptide, a protein, or an antibody, and at a dose of 0.01 ng/kg to 10 g/kg as an antisense oligonucleotide, siRNA, shRNAi, or miRNA.

As used herein, the term "subject" includes humans, orangutans, chimpanzees, mice, rats, dogs, cows, chickens, pigs, goats, sheep, and the like, but the present invention is not limited to the above examples.

In addition, the present invention relates to a method of providing information on the possibility of occurrence of non-alcoholic fatty liver by measuring a level of mRNA or the protein of the 14-3-3β gene and/or the 14-3-3γ gene from a sample of a patient suspected of having non-alcoholic fatty liver.

Specifically, the present invention provides a composition for diagnosing non-alcoholic fatty liver which includes a probe for measuring a level of mRNA or the protein of the 14-3-3β gene from a sample of a patient suspected of having non-alcoholic fatty liver.

The present invention also provides a composition for diagnosing non-alcoholic fatty liver which includes a probe for measuring a level of mRNA or the protein of the 14-3-3γ gene from a sample of a patient suspected of having non-alcoholic fatty liver.

In one embodiment, the probe for measuring a level of mRNA of the gene may be a nucleic acid probe or primer against the mRNA.

The nucleic acid probe refers to a natural or modified monomer or a linear oligomer having linkages that includes deoxyribonucleotides and ribonucleotides, which can be specifically hybridized with a target nucleotide sequence, and is occurring naturally or synthesized artificially. The probe according to the present invention may be in a single-stranded form, preferably, an oligodeoxyribonucleotide. The probe of the present invention may include natural dNMP (i.e., dAMP, dGMP, dCMP, and dTMP), or nucleotide analogs or derivatives. In addition, the probe of the present invention may also include ribonucleotides. For example, the probe of the present invention may include nucleotides with backbone modifications such as peptide nucleic acid (PNA), phosphorothioate DNA, phosphorodithioate DNA, phosphoroamidate DNA, amide-linked DNA, MMI-linked DNA, 2'-O-methyl RNA, alpha-DNA, and methylphosphonate DNA; nucleotides with sugar modifications such as 2'-O-methyl RNA, 2'-fluoro RNA, 2'-amino RNA, 2'-O-alkyl DNA, 2'-O-allyl DNA, 2'-O-alkynyl DNA, hexose DNA, pyranosyl RNA, and anhydrohexitol DNA; and nucleotides having base modifications such as C-5 substituted pyrimidines (substituents including fluoro-, bromo-, chloro-, iodo-, methyl-, ethyl-, vinyl-, formyl-, ethynyl-, propynyl-, alkynyl-, thiazolyl-, imidazolyl-, or pyridyl-), 7-deazapurines with C-7 substituents (substituents including fluoro-, bromo-, chloro-, iodo-, methyl-, ethyl-, vinyl-, formyl-, alkynyl-, alkenyl-, thiazolyl-, imidazolyl-, or pyridyl-), inosine, and diaminopurine.

The primer refers to a single-stranded oligonucleotide capable of initiating template-directed DNA synthesis in an appropriate buffer at an appropriate temperature under appropriate conditions (i.e., four different nucleoside triphosphates and a polymerase). An appropriate length of the primer may vary according to various factors, for example, temperature and the purpose of use thereof. In addition, a sequence of the primer does not need to be completely complementary to a part of the sequence of a template, but should be sufficiently complementary within a range enabling the primer to perform its intrinsic function by being hybridized with the template. Thus, the primer of the present invention does not need to have a sequence completely complementary to a nucleotide sequence of the gene as a template, but should be sufficiently complementary within a range enabling the primer to perform its function by being hybridized with the sequence of the gene. In addition, the primer according to the present invention may be used for gene amplification. The amplification refers to a reaction in which nucleic acid molecules are amplified, and such gene amplification is well known in the art, and includes, for example, polymerase chain reaction (PCR), reverse-transcription polymerase chain reaction (RT-PCR), ligase chain reaction (LCR), transcription mediated amplification (TMA), nucleic acid sequence-based amplification (NASBA), and the like.

In one embodiment, the probe for measuring a level of a protein may be an antibody against the protein.

As the antibody, a polyclonal antibody, a monoclonal antibody, a human antibody, a humanized antibody, or a fragment thereof may be used.

Examples of the fragment of the antibody includes Fab, Fab', F(ab')2, and Fv fragments; diabodies; linear antibodies; single-chain antibody molecules; multispecific antibodies formed from antibody fragments; and the like.

When an antibody is digested with papain, two identical antigen-binding fragments, i.e., each a "Fab" fragment with a single antigen binding site, and the remainder, a "Fc" fragment, are produced. When an antibody is treated with pepsin, a F(ab') fragment having two antigen binding sites and still capable of cross-linking with an antigen is produced. Fv is the minimal antibody fragment containing a complete antigen recognition and binding site. The Fv fragment consists of a dimer of one heavy chain variable domain and one light chain variable domain via tight non-covalent binding.

A polyclonal antibody production method is known in the art. A polyclonal antibody may be produced by injecting an immunizing agent into a mammal once or more, or in combination with an adjuvant when necessary. Generally, an immunizing agent and/or an adjuvant is/are injected into a mammal several times via subcutaneous injection or intra-peritoneal injection. The immunizing agent may be the protein of the present invention or a fusion protein thereof. It may be effective to inject an immunizing agent in combination with a protein known to have immunogenicity in a mammal to be immunized.

The monoclonal antibody according to the present invention may be produced using a hybridoma method described in a document (Kohler et al., Nature, 256:495 (1975)), or using a recombinant DNA method (e.g., see U.S. Pat. No. 4,816,576). In addition, for example, the monoclonal antibody may be isolated from a phage antibody library using a technique described in a document (Clackson et al., *Nature,* 352:624-628 (1991) and Marks et al., *J. Mol. Biol.,* 222: 581-597 (1991)).

In particular, the monoclonal antibody of the present invention includes "chimeric" antibodies, in which part of the heavy chain and/or light chain has a sequence identical or homologous to the corresponding sequence of an antibody derived from a specific species or belonging to a specific antibody class or subclass, while the remaining chain(s) is/are identical or homologous to an antibody derived from another species or an antibody belonging to another antibody class or subclass or a fragment thereof, so long as they exhibit desired activities.

"Humanized" forms of non-human (e.g., murine) antibodies are chimeric immunoglobulins containing the minimum sequence derived from non-human immunoglobulins, immunoglobulin chains, or fragments thereof (e.g., Fv, Fab, Fab', F(ab')2 or other antigen binding sequences of antibodies). In most cases, humanized antibodies include human immunoglobulins (recipient antibody) in which residues of the complementarity determining region (CDR) of a recipient are substituted with CDR residues of a non-human species (donor antibody) such as mice, rats, or rabbits having desired specificity, affinity, and capability. In some cases, Fv framework residues of a human immunoglobulin are substituted with corresponding non-human residues. In addition, humanized antibodies may include residues that are not found in a recipient antibody, or an introduced CDR or framework sequence. Generally, a humanized antibody substantially includes one or more, generally, two or more variable domains, and, as used herein, all or substantially all CDRs correspond to regions of a non-human immunoglobulin, and all or substantially all FRs correspond to regions of a human immunoglobulin sequence. In addition, the humanized antibody includes at least a part of immunoglobulin constant region (Fc), generally, a part of a human immunoglobulin region.

The composition for diagnosing non-alcoholic fatty liver of the present invention may be included in the form of a kit.

The kit may include a primer, probe or antibody capable of measuring an expression level of the 14-3-3β gene or the 14-3-3γ gene or an amount of the protein thereof, and the definitions of these are the same as described above.

When applied to a PCR amplification process, the kit may optionally include reagents needed for PCR amplification, for example, a buffer, a DNA polymerase (e.g., a thermally stable DNA polymerase obtained from *Thermus aquaticus* (Taq), *Thermus thermophilus* (Tth), *Thermus filiformis*, *Thermis flavus*, *Thermococcus literalis*, or *Pyrococcus furiosus* (Pfu)), a DNA polymerase cofactor, and dNTPs. When applied to an immunoassay, the kit of the present invention may optionally include a secondary antibody and a marker substrate. Furthermore, the kit according to the present invention may be constructed as separate multiple packages or compartments including the reagent components.

In addition, the composition for diagnosing non-alcoholic fatty liver of the present invention may be included in the form of a microarray.

In the microarray of the present invention, the primer, probe or antibody capable of measuring an expression level of the 14-3-3β or 14-3-3γ protein or a gene encoding the same is used as a hybridizable array element, and is immobilized on a substrate. Preferable substrates may include suitable rigid or semi-rigid supports, for example, films, filters, chips, slides, wafers, fibers, magnetic beads or non-magnetic beads, gels, tubing, plates, polymers, microparticles, and capillaries. The hybridizable array element is arranged and immobilized on the substrate, and such immobilization may be performed by a chemical binding method or a covalent binding method, such as using UV. For example, the hybridizable array element may be bound to a glass surface that is modified to contain an epoxy compound or an aldehyde group, or may be bound to a polylysine-coated surface by UV. In addition, the hybridizable array element may be bound to a substrate via a linker (e.g., an ethylene glycol oligomer and a diamine).

Meanwhile, when a sample applied to the microarray of the present invention is nucleic acid, the nucleic acid may be labeled and hybridized with an array element on the microarray. Hybridization conditions may vary, and detection and analysis of a hybridization degree may be variously performed according to a marker.

The present invention also provides a method of providing information needed to diagnose non-alcoholic fatty liver through a method of measuring an expression level of the 14-3-3β gene or the 14-3-3γ gene or a level of an expression protein thereof. More specifically, the method may include: (a) measuring an expression level of the 14-3-3β gene or the 14-3-3γ gene or an amount of an expression protein thereof from a biological sample of a patient suspected of having non-alcoholic fatty liver; and (b) measuring an expression level of the gene or an amount of an expression protein thereof from a normal control sample and comparing measurement results with that of process (a).

The method of measuring an expression level of the gene or an amount of the protein thereof may be performed using a known technique including a known process of isolating mRNA or protein from a biological sample.

The biological sample refers to a sample collected from a living body, wherein the sample has a different expression level of the gene or a different level of the protein thereof according to occurrence or progression degree of non-alcoholic fatty liver from that of a normal control, and the sample may include, but is not limited to, for example, tissue, cells, blood, serum, plasma, saliva, urine, and the like.

The measurement of an expression level of the gene is preferably measurement of a level of mRNA, and a method of measuring a level of mRNA may be reverse transcription polymerase chain reaction (RT-PCR), real-time reverse transcription polymerase chain reaction, RNase protection assay, northern blotting, DNA chips, or the like, but is not limited thereto.

The measurement of a level of the protein thereof may be performed using an antibody, and in this case, the protein in a biological sample and an antibody specific thereto form a resulting material, i.e., an antigen-antibody complex, and an amount of the formed antigen-antibody complex may be quantitatively measured through a size of signal of a detection label. Such a detection label may be selected from the group consisting of enzymes, fluorescent materials, ligands, luminescent materials, microparticles, redox molecules, and radioactive isotopes, but is not limited to the above examples. An analysis method for measuring the level of protein may be, but is not limited to, western blotting, enzyme linked immunosorbent assay (ELISA), radioimmunoassay, radioimmunodiffusion, Ouchterlony immunodiffusion, rocket immunoelectrophoresis, immunohistostaining, immunoprecipitation assay, complement fixation assay, fluorescence activated cell sorting (FACS), a protein chip, or the like.

Thus, in the present invention, through the above-listed detection methods, an expression amount of mRNA and an amount of a protein of a control and an expression amount of mRNA and an amount of the protein of a patient suspected of having non-alcoholic fatty liver may be identified, and the occurrence, progression stage, and the like of non-alcoholic fatty liver may be diagnosed by comparing a degree of the expression amount of the patient with that of the control.

In addition, according to the method of providing information for the diagnosis of non-alcoholic fatty liver, when an expression level of the 14-3-3β gene according to the present invention or an amount of an expression protein thereof is increased compared to that of a normal control sample, it may be determined that non-alcoholic fatty liver is induced or highly likely to develop. On the other hand, when the expression level of the 14-3-3γ gene or the amount of an expression protein thereof is decreased compared to that of the normal control sample, it may be determined that non-alcoholic fatty liver is induced or highly likely to develop.

The present invention also provides a method of screening a drug for the prevention or treatment of fatty liver, including: bringing a cell containing the 14-3-3β gene or the 14-3-3γ gene, or the protein thereof into contact with a candidate material in vitro; and measuring a change in expression amount of the gene or the protein by the candidate material.

For example, when the candidate material downregulates the expression of the 14-3-3β gene or the protein thereof, the candidate material may be determined as a drug for the prevention or treatment of fatty liver. On the other hand, when the candidate material upregulates expression of the 14-3-3γ gene or the protein thereof, the candidate material may be determined as a drug for the prevention or treatment of fatty liver.

The present invention also provide a method of screening a drug for the prevention or treatment of fatty liver, including bringing the 14-3-3β protein and/or the 14-3-3γ protein into contact with a candidate material as well as the PPARγ$_2$ protein and measuring a change in binding of the 14-3-3β protein and/or the 14-3-3γ protein to PPARγ$_2$ by the candidate material.

In one embodiment, measurement of the change in binding of the 14-3-3β protein and/or the 14-3-3γ protein to PPARγ$_2$ by the candidate material may be performed by measuring a change in binding of the 14-3-3β protein and/or the 14-3-3γ protein to the Ser273 residue of PPARγ$_2$.

The candidate material may be, according to a general selection method, a substance that accelerates or suppresses transcription and translation of 14-3-3β and/or a 14-3-3γ gene base sequence into mRNA and proteins, or individual nucleic acids, proteins, peptides, extra extracts or natural substances, compounds, and the like that are assumed to have potential as a drug that enhances or inhibits a function or activity of 14-3-3β and/or 14-3-3γ or are randomly selected.

Subsequently, an expression amount of the gene, an amount of the protein, or an activity of the protein may be measured in cells treated with the candidate material, and, as a result of measurement, when the expression amount of the gene, the amount of the protein, or the activity of the protein is increased or decreased, the candidate material may be determined as a material capable of preventing or treating fatty liver.

The measurement of the expression amount of the gene, the amount of the protein, or the activity of the protein may be performed using various methods known in the art, and examples of measurement methods thereof include, but are not limited to, reverse transcriptase-polymerase chain reaction, real time-polymerase chain reaction, western blotting, northern blotting, enzyme linked immunosorbent assay (ELISA), radioimmunoassay (RIA), radioimmunodiffusion, and immunoprecipitation assay.

A candidate material that inhibits/enhances expression of the 14-3-3β gene and/or the 14-3-3γ gene or exhibits an activity of inhibiting/enhancing a function of the protein thereof, obtained through the screening method of the present invention, may be a candidate material for a drug for the prevention or treatment of fatty liver.

Such a candidate material for a drug for the prevention or treatment of fatty liver acts as a leading compound in a subsequent process of developing a therapeutic agent, and a structure of the leading compound may be modified and optimized to exhibit an effect of promoting or inhibiting a function of the 14-3-3β gene and/or the 14-3-3γ gene or the protein expressed therefrom, and, accordingly, a novel fatty liver therapeutic agent may be developed.

Hereinafter, the present invention will be described in detail with reference to the following examples. However, these examples are provided for illustrative purposes only and are not intended to limit the scope of the present invention.

EXPERIMENTAL MATERIALS

Dulbecco's modified Eagle's medium (DMEM), Medium 199 (M199), fetal bovine serum (FBS), penicillin, streptomycin, and Opti-MEM were purchased from Invitrogen (Carlsbad, Calif.).

si-14-3-3β and si-14-3-3γ siRNA, anti-PPARγ, anti-GFP, anti-GST, anti-Flag, anti-p-Cdk5(Tyr15), anti-Cdk5 and anti-HA, anti-SREBP-1c antibodies, and Roscovitine were purchased from Santa Cruz Biotechnology (Santa Cruz, Calif., USA), and anti-p-PPARγ$_2$(Ser273) antibodies were purchased from Rockland Immunochemicals Inc. (Limerick, Pa., USA).

An E-fection plus reagent was purchased from Lugen Sci. (Seoul, South Korea).

A luciferase analysis system was purchased from Promega Co. (Madison, Wis., USA).

Pioglitazone and oleic acid were purchased from Sigma (St. Louis, Mo., USA).

A triglyceride analysis system was purchased from Cayman Chemical (Ann Arbor, Mich., USA).

<Example 1> Identification of 14-3-3β and 14-3-3γ Regulating Transcriptional Activity of PPARγ$_2$ The transcriptional activity of PPARγ$_2$ plays a vital role in expression of liver diseases-associated proteins. Thus, the transcriptional activity of PPARγ$_2$ was measured using an aP2 promoter regulated by PPARγ$_2$, and the role of 7 types of 14-3-3 proteins was investigated.

For this, HEK-293T cells were seeded in a 12-well plate at a density of 1×10$^5$ cells per each well, and then transfected with an aP2 promoter construct (0.5 μg) and 14-3-3 isoform proteins (α, β, γ, δ, ε, ζ, η, θ) (0.5 μg) or si-14-3-3β and si-14-3-3γ siRNA (5 nM and 10 nM, Santa Cruz) using an E-fection plus reagent (Lugen). A ratio of DNA to the E-fection plus reagent was 1:2, and this method was performed according to a manufacturer's manual. After transfection, the corresponding cells were treated with 10 μM of pioglitazone (Pio, Santa Cruz) for 24 hours, washed with ice-cold PBS, and lysed using 80 μl/well of a reporter lysis buffer (Promega, Madison, Wis.), and the lysed cells were centrifuged at 10,000×g and 4° C. for 10 minutes to collect a supernatant, and luciferase activity was measured. As an instrument, Luminometer 20/20n (Turner Biosystems, Sunnyvale, Calif.) was used. For normalization, the cells were cotransfected with pSV40-β-galactosidase. For the collected supernatant, β-galactosidase activity was measured and the luciferase activity was revised, and the obtained values were plotted. At this time, a β-galactosidase enzyme analysis system (Promega, Madison, Wis.) was used, and analysis was performed using a DU530 spectrophotometer (Beckman Instruments, Palo Alto, Calif.).

As a result of measuring activity of the aP2 promoter, it was confirmed that 14-3-3β increased the transcriptional activity of PPARγ$_2$, and 14-3-3γ decreased the transcriptional activity of PPARγ$_2$. However, there were no changes in the other 5 types of isoform proteins (see FIG. 1A).

Figure 1B:
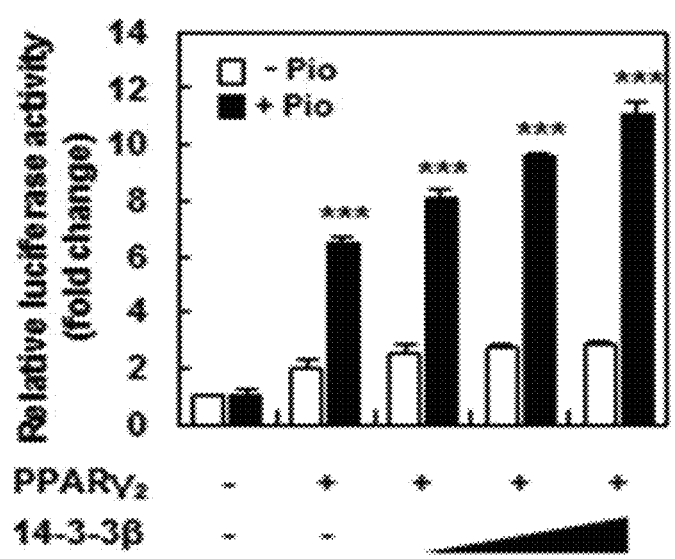
FIG. 1B illustrates results of verifying the transcriptional activity of PPAR$\gamma_2$ according to a change in the expression amount of 14-3-3$\beta$.
Figure 1C:
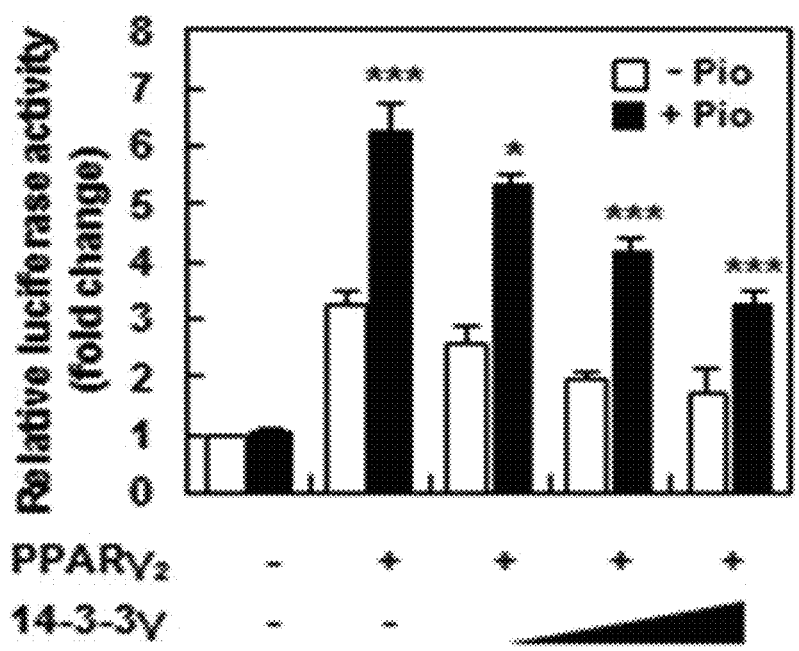
FIG. 1C illustrates results of verifying the transcriptional activity of PPAR$\gamma_2$ according to a change in the expression amount of 14-3-3$\gamma$.

To accurately verify whether 14-3-3β and 14-3-3γ are involved in the transcriptional activity of PPARγ$_2$, 14-3-3β and 14-3-3γ were overexpressed according to concentration and, as a result of measurement, 14-3-3β increased the transcriptional activity of PPARγ$_2$ in a concentration-dependent manner (see FIG. 1B). However, 14-3-3γ reduced the transcriptional activity of PPARγ$_2$ in a concentration-dependent manner (see FIG. 1C).

Figure 1D:
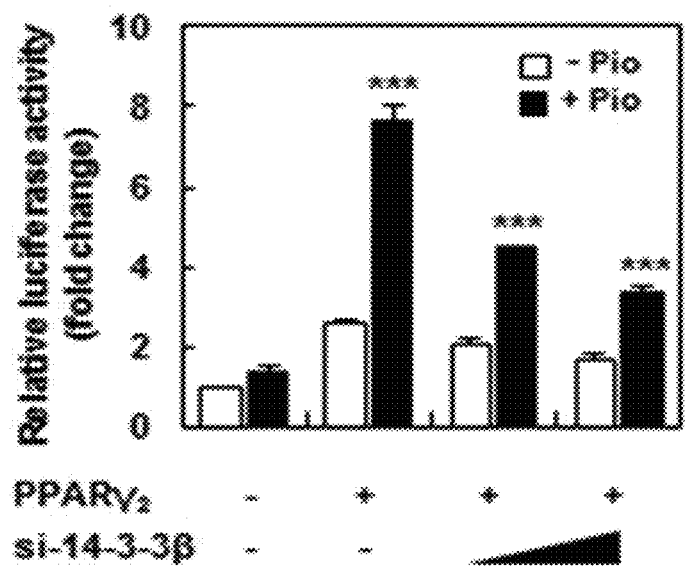
FIG. 1D illustrates results of verifying the transcriptional activity of PPAR$\gamma_2$ according to the inhibition of 14-3-3$\beta$ expression.
Figure 1E:
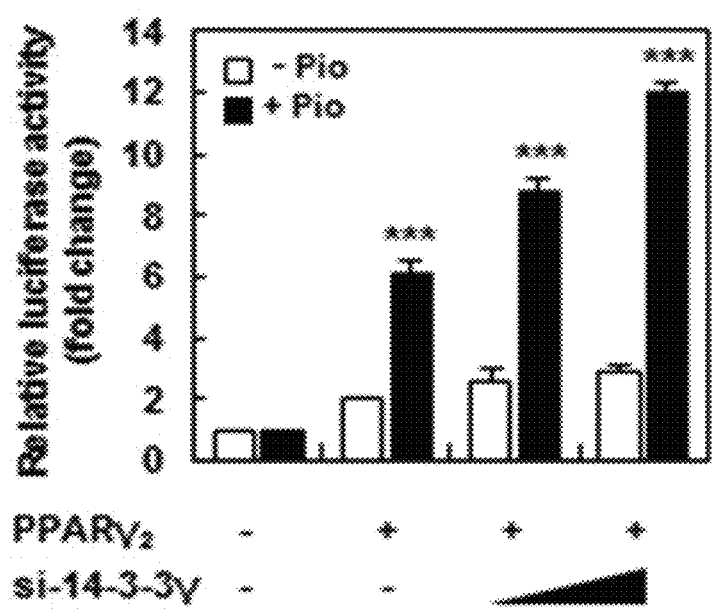
FIG. 1E illustrates results of verifying the transcriptional activity of PPAR$\gamma_2$ according to the inhibition of 14-3-3$\gamma$ expression.

On the other hand, when the expression of 14-3-3β was inhibited using si-14-3-3β, the transcriptional activity of PPARγ$_2$ was decreased (see FIG. 1D), and, when the expression of 14-3-3γ was inhibited, the transcriptional activity of PPARγ$_2$ was increased (see FIG. 1E).

Thus, according to the present experimental results, it is determined that 14-3-3β is involved in increasing the transcriptional activity of PPARγ$_2$, and 14-3-3γ plays a role in inhibiting the transcriptional activity of PPARγ$_2$, and 14-3-3β and 14-3-3γ are genes that regulate in opposite manners.

<Example 2> Verification of Binding of 14-3-3β and 14-3-3γ to PPARγ$_2$

From the transcriptional activity experimental results, 14-3-3β and 14-3-3γ were seen to regulate the transcriptional activity of PPARγ$_2$, and thus it was assumed that 14-3-3β and 14-3-3γ could bind to PPARγ$_2$.

Thus, it was investigated by GST-pull down assay whether 14-3-3β and 14-3-3γ bind to PPARγ$_2$.

For this, HEK-293T cells were seeded in a 100 mm plate at a density of 2×10$^6$ cells per each well, and then transfected with Myc-PPARγ$_2$ DNA (4 μg) and mGST-14-3-3β (4 μg) or mGST-14-3-3γ (4 μg) using an E-fection plus reagent (Lugen). A ratio of DNA to the E-fection plus reagent was 1:2, and this method was performed according to a manufacturer's manual. After transfection, the corresponding cells were treated with 10 μM of pioglitazone (Pio, Santa Cruz) for 24 hours, washed with ice-cold PBS, and lysed using 500 μl/well of a lysis buffer (150 mM NaCl, 1 mM EDTA, 1% Nonidet P-40, 5% glycerol, 25 mM tris-HCl, pH 7.5, protease inhibitor added), and the lysed cells were centrifuged at 10,000×g and 4° C. for 10 minutes to extract proteins. Thereafter, 1,000 μg of the proteins was reacted with 20 μl of glutathione Sepharose 4B beads (GE Healthcare, Buckinghamshire, UK) for 6 hours, and then washing of the beads with 1 ml of ice-cold PBS was repeated 5 times, and the beads were boiled at 100° C. for 10 minutes, followed by 10% SDS-PAGE gel separation and western blotting. A ratio of GST antibodies (Santa Cruz) to Myc antibodies (self-production) was 1:3000. The detection of each protein was performed using West Pico ECL (Thermo scientific, Rockford, Ill.) and identified in a darkroom.

Figure 2A:
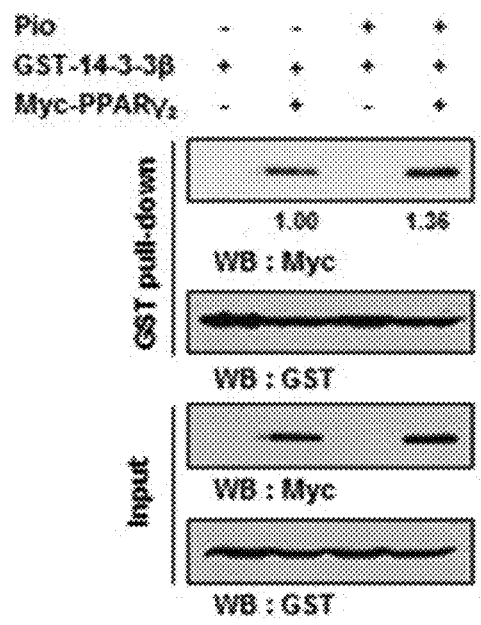
Figure 2B:
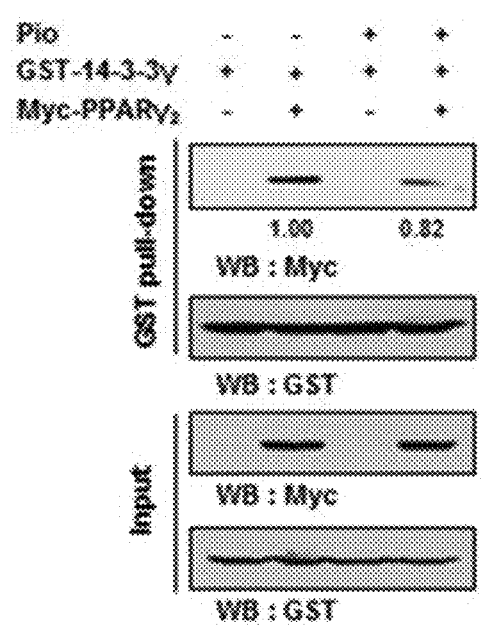

As a result, binding between PPARγ$_2$ and 14-3-3β became stronger when pioglitazone, which is a PPARγ$_2$ ligand, was treated (see FIG. 2A). In contrast to 14-3-3β, binding between PPARγ$_2$ and 14-3-3γ was reduced (see FIG. 2B). From these results, it was determined that, when the activation of PPARγ$_2$ proceeds, binding of PPARγ$_2$ with 14-3-3β increases, and binding thereof with 14-3-3γ decreases, and thus the expression of a target gene is regulated by regulating the transcriptional activity of PPARγ$_2$ by these two proteins.

Figure 3A:
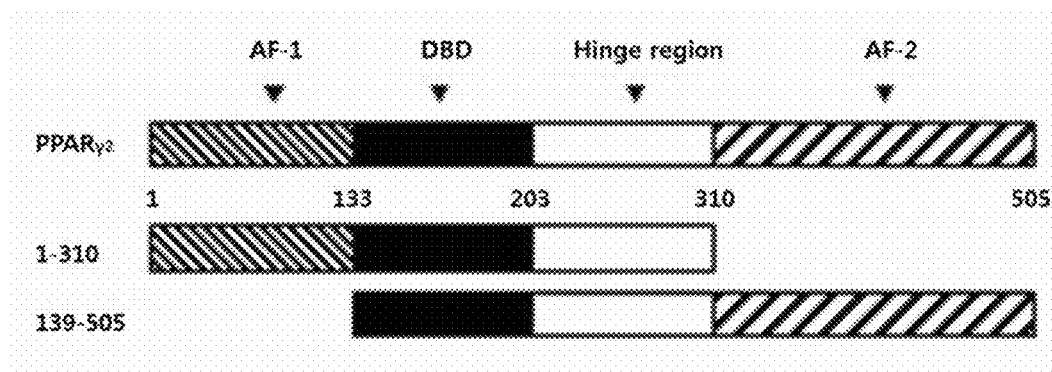
FIG. 3A illustrates verification results of a domain position and deletion mutation of PPAR$\gamma_2$.

<Example 3> Verification of Domain in which 14-3-3β and 14-3-3γ Bind to PPARγ$_2$ The PPARγ$_2$ protein has been reported to consist of an activation function 1 (AF-1, amino acids 1-138) domain, a DNA-binding domain (DBD, amino acids 139-203), a hinge region (amino acids 204-310), and an activation function 2 (AF-2, amino acids 311-505) domain (see FIG. 3A). Thus, GST-pull down assay was conducted to verify which domain part of PPARγ$_2$ was bound to 14-3-3β and 14-3-3γ.

HEK-293T cells were seeded in a 100 mm plate at a density of 2×10$^6$ cells per each well, and then transfected with Flag-PPARγ$_2$ (1-505) DNA (4 μg), Flag-PPARγ$_2$ (1-310) DNA (4 μg), Flag-PPARγ$_2$ (139-505) DNA (4 μg), and mGST-14-3-3β (4 μg) or mGST-14-3-3γ (4 μg) using an E-fection plus reagent (Lugen). For Flag-PPARγ$_2$ (1-310) DNA and Flag-PPARγ$_2$ (139-505) DNA, DNA fragments amplified through polymerase chain reaction (PCR) were cloned into a pCMV-3Tag-1 vector using restriction enzymes XhoI and ApaI. A ratio of DNA to the E-fection plus reagent was 1:2, and this method was performed according to a manufacturer's manual. The corresponding cells were washed with ice-cold PBS and lysed using 500 μl/well of a lysis buffer (150 mM NaCl, 1 mM EDTA, 1% Nonidet P-40, 5% glycerol, 25 mM tris-HCl, pH 7.5, protease inhibitor added), and the lysed cells were centrifuged at 10,000×g and 4° C. for 10 minutes to extract proteins. Thereafter, 1,000 μg of the proteins was reacted with 20 μl of glutathione Sepharose 4B beads (GE Healthcare, Buckinghamshire, UK) for 6 hours, and then washing of the beads with 1 ml of ice-cold PBS was repeated 5 times, and the beads were boiled at 100° C. for 10 minutes, followed by 10% SDS-PAGE gel separation and western blotting. A ratio of GST antibodies (Santa Cruz) to Flag antibodies (Santa Cruz) was 1:3000. The detection of each protein was performed using West Pico ECL (Thermo scientific, Rockford, Ill.) and identified in a darkroom.

Figure 3B:
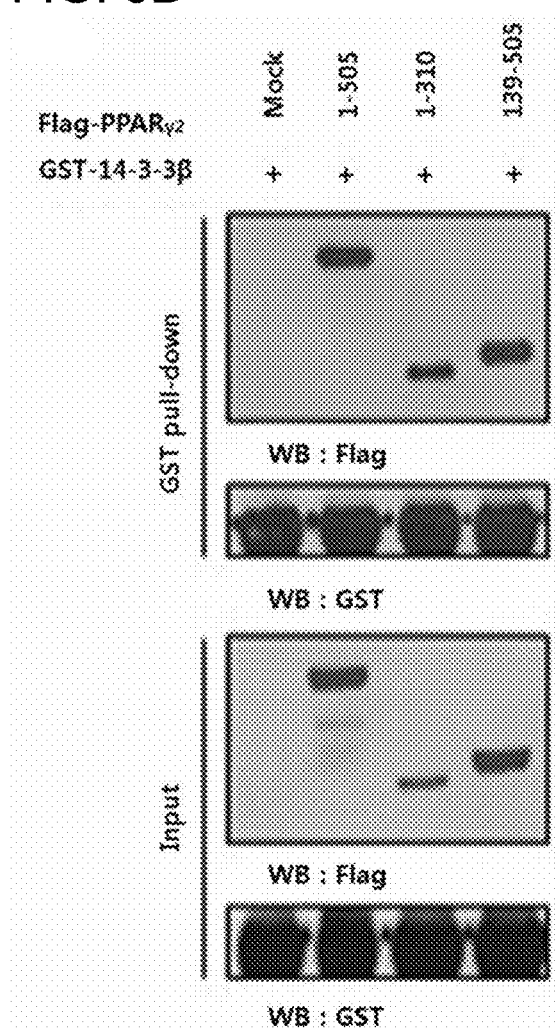
FIG. 3B illustrates verification results of deletion mutation of PPAR$\gamma_2$ and binding between the deletion mutants and 14-3-3$\beta$ by GST-pull down assay.

As a result of verifying binding between the wild-type and two deletion mutants of the PPARγ$_2$ gene and 14-3-3β or 14-3-3γ, each of 14-3-3β (see FIG. 3B) and 14-3-3γ (see FIG. 3C) is bound to a PPARγ$_2$ deletion mutant (1-310) and a PPARγ$_2$ deletion mutant (139-505). These results indicate binding between 14-3-3β or 14-3-3γ and the DBD or hinge region of PPARγ$_2$.

<Example 4> Verification of Residues of PPARγ$_2$ to which 14-3-3β and 14-3-3γ Bind 14-3-3 proteins are known to bind to phosphorylated residues of a target protein. Phosphorylated residues associated with the activity of PPARγ$_2$ are known to be serine 112 and serine 273. Thus, PPARγ$_2$ mutants (PPARγ$_2$ S112A and S273A) with non-phosphorylated serine 112 and serine 273 residues were produced and binding thereof with 14-3-3 proteins was verified through GST-pull down assay.

HEK-293T cells were seeded in a 100 mm plate at a density of 2×10$^6$ cells per each well, and then transfected with Flag-PPARγ$_2$ (WT) DNA (4 μg), Flag-PPARγ$_2$ (S112A) DNA (4 μg), Flag-PPARγ$_2$ (S273A) DNA (4 μg), and mGST-14-3-3β (4 μg) or mGST-14-3-3γ (4 μg) using an E-fection plus reagent (Lugen). As for Flag-PPARγ$_2$ (S112A) DNA and Flag-PPARγ$_2$ (S273A) DNA, DNA fragments amplified through polymerase chain reaction (PCR) were cloned into a Flag-tagged vector. A ratio of DNA to the E-fection plus reagent was 1:2, and this method was performed according to a manufacturer's manual. The corresponding cells were washed with ice-cold PBS and lysed using 500 μl/well of a lysis buffer (150 mM NaCl, 1 mM EDTA, 1% Nonidet P-40, 5% glycerol, 25 mM tris-HCl, pH 7.5, protease inhibitor added), and the lysed cells were centrifuged at 10,000×g and 4° C. for 10 minutes to extract proteins. Thereafter, 1,000 μg of the proteins was reacted with 20 μl of glutathione Sepharose 4B beads (GE Healthcare, Buckinghamshire, UK) for 6 hours, and then washing of the beads with 1 ml of ice-cold PBS was repeated 5 times, and the beads were boiled at 100° C. for 10 minutes, followed by 10% SDS-PAGE gel separation and western blotting. A ratio of GST antibodies (Santa Cruz) to Flag antibodies (Santa Cruz) was 1:3000. The detection of each protein was performed using West Pico ECL (Thermo scientific, Rockford, Ill.) and identified in a darkroom.

In addition, HEK-293T cells were seeded in a 12-well plate at a density of $1 \times 10^5$ cells per each well, and then transfected with an aP2 promoter construct (0.5 µg), Flag-PPARγ$_2$ (S112A) DNA (0.5 µg) or Flag-PPARγ$_2$ (S273A) DNA (0.5 µg), and mGST-14-3-3β DNA (0.5 µg) or mGST-14-3-3γ DNA (0.5 µg) using an E-fection plus reagent (Lugen). A ratio of DNA to the E-fection plus reagent was 1:2, and this method was performed according to a manufacturer's manual. The corresponding cells were washed with ice-cold PBS, and lysed using 80 µl/well of a reporter lysis buffer (Promega, Madison, Wis.), and the lysed cells were centrifuged at 10,000×g and 4° C. for 10 minutes to collect a supernatant, and luciferase activity was measured. As an instrument, Luminometer 20/20n (Turner Biosystems, Sunnyvale, Calif.) was used. For normalization, the cells were cotransfected with pSV40-β-galactosidase. For the collected supernatant, β-galactosidase activity was measured and the luciferase activity was revised, and the obtained values were plotted. At this time, a β-galactosidase enzyme analysis system (Promega, Madison, Wis.) was used, and analysis was performed using a DU530 spectrophotometer (Beckman Instruments, Palo Alto, Calif.).

Figure 4A:
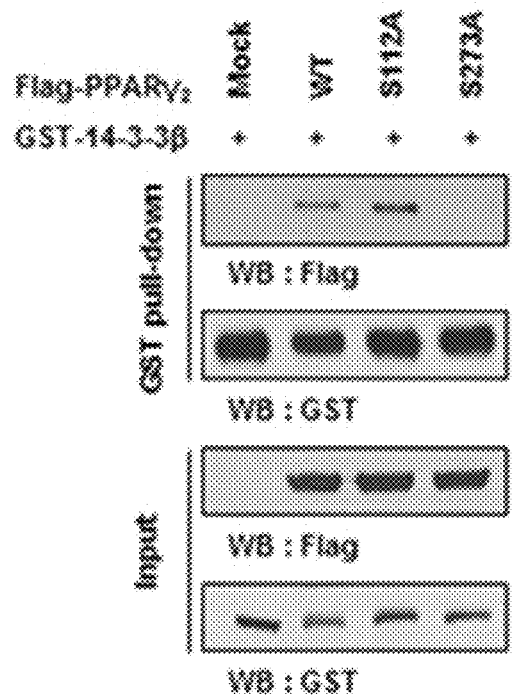
FIG. 4A illustrates verification results of S112A and S273A mutations of PPARγ$_2$ and binding between the mutants and 14-3-3β.
Figure 4B:
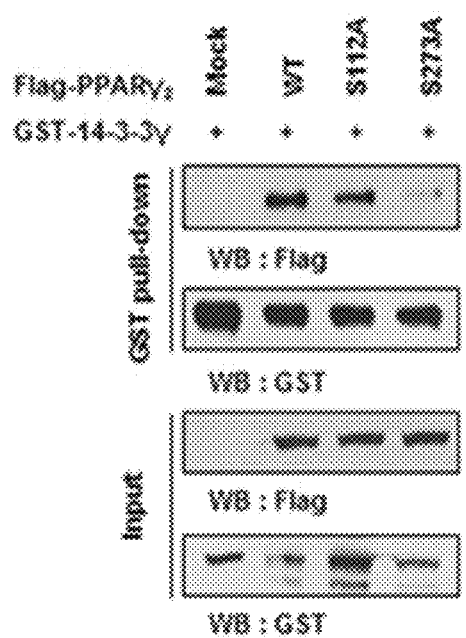
FIG. 4B illustrates verification results of S112A and S273A mutations of PPARγ$_2$ and binding between the mutants and 14-3-3γ.
Figure 4C:
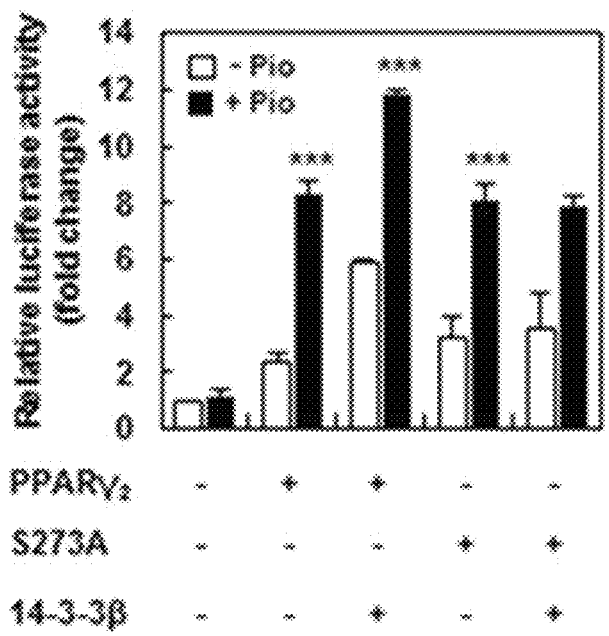
FIG. 4C illustrates verification results of the transcriptional activity of PPARγ$_2$ according to binding between S273A mutant of PPARγ$_2$, and 14-3-3β.
Figure 4D:
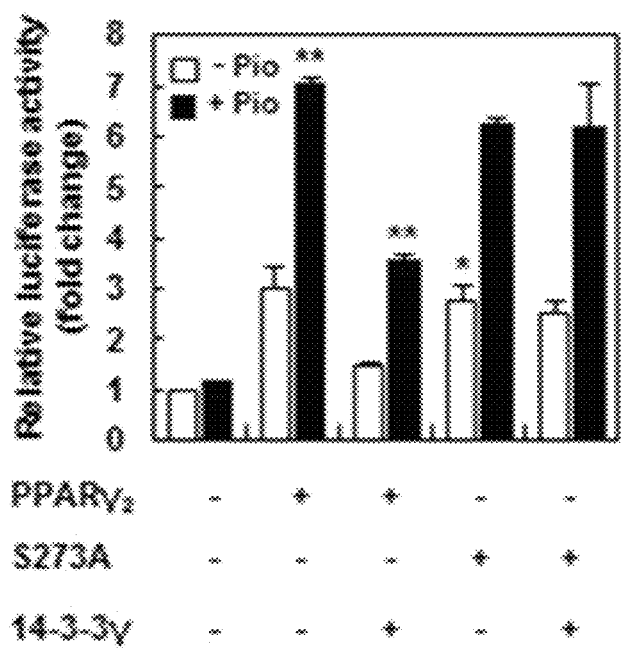
FIG. 4D illustrates verification results of the transcriptional activity of PPARγ$_2$ according to binding between S273A mutant of PPARγ$_2$, and 14-3-3γ.

As a result, both binding with 14-3-3β and binding with 14-3-3γ were suppressed in the PPARγ$_2$ S273A mutant (see FIGS. 4A and 4B). In addition, there was no change in the transcriptional activity of PPARγ$_2$, increased according to overexpression of 14-3-3β, in the case of the PPARγ$_2$ S273A mutant (see FIG. 4C). In addition, there was no change in the transcriptional activity of PPARγ$_2$, reduced when 14-3-3γ was overexpressed, in the case of the PPARγ$_2$ S273A mutant (see FIG. 4D). Thus, it was verified that 14-3-3β and 14-3-3γ were bound to the serine 273 residue of PPARγ$_2$, thereby regulating the transcriptional activity of PPARγ$_2$.

<Example 5> Verification of Competitive Binding of 14-3-3β and 14-3-3γ with PPARγ$_2$ From the previous experimental results, it was verified that 14-3-3β and 14-3-3γ were bound to the phosphorylated serine 273 residue of PPARγ$_2$, and it was determined that the two proteins would competitively bind to the same residue. Thus, GST-pull down assay was carried out to verify competitive binding of 14-3-3β and 14-3-3γ with PPARγ$_2$.

HEK-293T cells were seeded in a 100 mm plate at a density of $2 \times 10^6$ cells per each well, and then transfected with mGST-PPARγ$_2$ DNA (4 µg), GFP-14-3-3β DNA (4 µg) or GFP-14-3-3γ DNA (4 µg), and HA-14-3-3β DNA (2 and 4 µg) or HA-14-3-3γ DNA (2 and 4 µg) using an E-fection plus reagent (Lugen). A ratio of DNA to the E-fection plus reagent was 1:2 and this method was performed according to a manufacturer's manual. After transfection, the corresponding cells were treated with 10 µM of pioglitazone (Pio, Santa Cruz) for 24 hours, washed with ice-cold PBS, and lysed using 500 µl/well of a lysis buffer (150 mM NaCl, 1 mM EDTA, 1% Nonidet P-40, 5% glycerol, 25 mM tris-HCl, pH 7.5, protease inhibitor added), and the lysed cells were centrifuged at 10,000×g and 4° C. for 10 minutes to extract proteins. Thereafter, 1,000 µg of the proteins was reacted with 20 µl of glutathione Sepharose 4B beads (GE Healthcare, Buckinghamshire, UK) for 6 hours, and then washing of the beads with 1 ml of ice-cold PBS was repeated 5 times, and the beads were boiled at 100° C. for 10 minutes, followed by separation on a 10% SDS-PAGE gel. The proteins were identified using each of a plurality of antibodies (GST, GFP, HA: Santa Cruz) by western blotting, and all antibodies were used in a ratio of 1:3000.

Figure 5A:
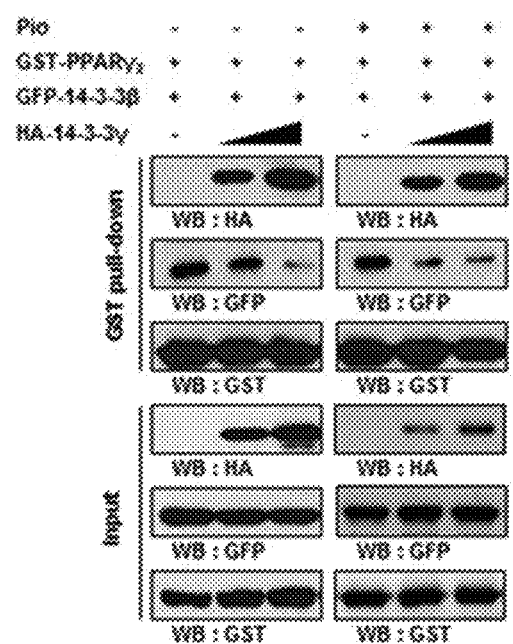
Figure 5B:
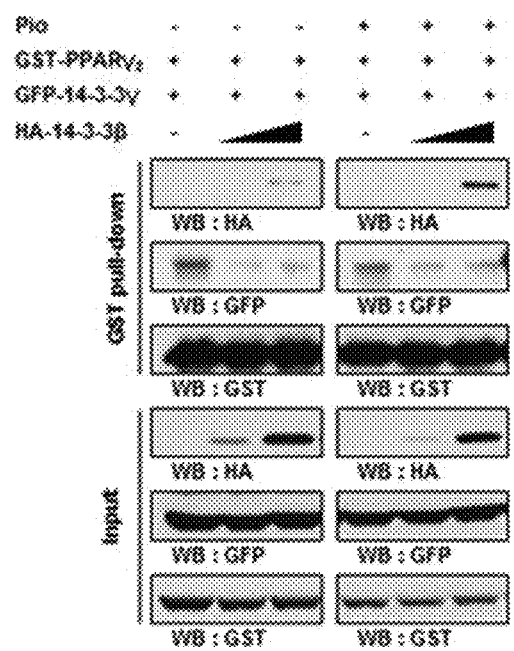

As a result, as an expression amount of 14-3-3γ was increased, binding between 14-3-3β and PPARγ$_2$ was reduced (see FIG. 5A), and, as an expression amount of 14-3-3β was increased, binding between 14-3-3γ and PPARγ$_2$ was reduced (see FIG. 5B). This indicates that 14-3-3β and 14-3-3γ competitively bind to the phosphorylated serine 273 residue of PPARγ$_2$.

<Example 6> Increase in Expression of PPARγ$_2$ by Oleic Acid and Regulation of Expression of PPARγ$_2$ Target Gene Thereby It is known that, in the liver of obese mice, the expression and activity of PPARγ$_2$ are increased, and the expression of a target gene thereof is increased. To form such an obese environment in an in vitro experiment, mRNA expression amounts of PPARγ$_2$, and 14-3-3β and 14-3-3γ were checked through treatment with oleic acid (OA), which is a type of fatty acid.

HepG2 cells and primary mouse hepatocytes were separately seeded in a 6-well plate at a density of $4 \times 10^5$ cells per each well, and then treated with 200 µM of oleic acid (OA) for 72 hours. For mRNA extraction, the corresponding cells were lysed with 1 ml/well of TRIzol (Invitrogen), 200 µl of chloroform was added thereto and mixed well, the resultant cells were maintained at room temperature for 5 minutes and then centrifuged at 12,000×g and 4° C. for 15 minutes, the obtained supernatant was mixed with 500 µl of isopropanol and then put on ice for 10 minutes, the resulting supernatant was centrifuged at 12,000×g and 4° C. for 15 minutes to remove a supernatant, and then pellets were dissolved with tertiary distilled water treated with diethyl pyrocarbonate (DEPC). 2 µg of mRNA was synthesized into cDNA using a Superscript First Strand cDNA Synthesis Kit (Bioneer, Daejeon, South Korea) and the synthesized cDNA as a template was amplified through polymerase chain reaction (PCR) using primers specific to PPARγ$_2$, 14-3-3β, 14-3-3γ, SREBP-1c, SCD-1, ACC, FABP, FAT/CD36, and β-actin of humans, and was amplified through real-time PCR using primers specific to PPARγ$_2$, 14-3-3β, 14-3-3γ, SREBP-1c, FAT/CD36, and GAPDH of mice. β-actin and GAPDH were used as controls to see whether mRNAs of the respective cells were compared in the same amount.

Figure 6A:
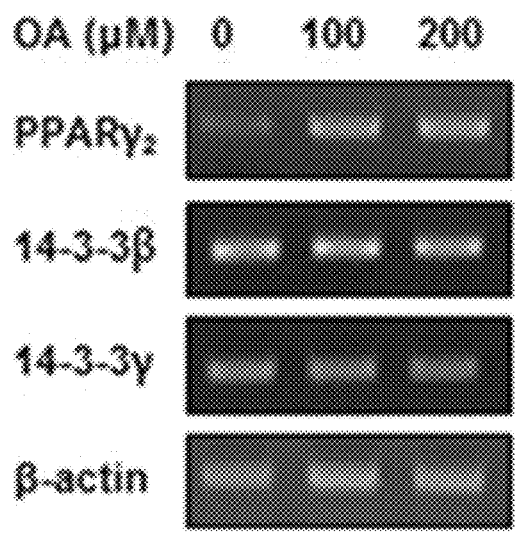
FIG. 6A illustrates verification results of the expression of PPARγ$_2$, 14-3-3β, and 14-3-3γ in HepG2 cells according to oleic acid treatment.
Figure 6B:
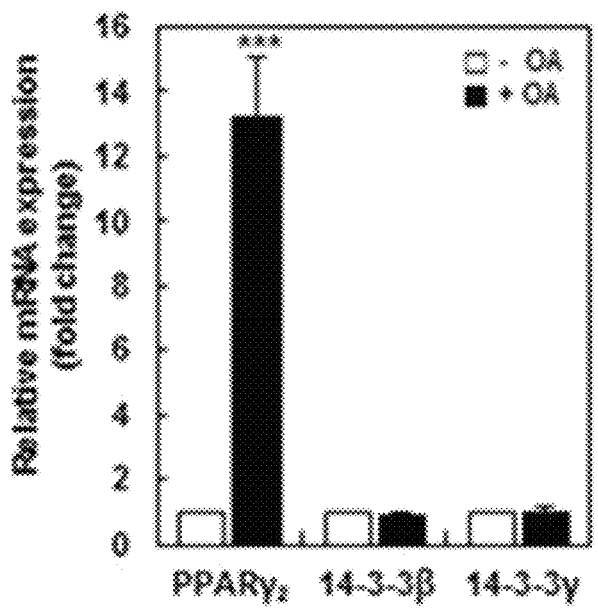
FIG. 6B illustrates verification results of the expression of PPARγ$_2$, 14-3-3β, and 14-3-3γ in primary mouse hepatocytes according to oleic acid treatment.
Figure 6C:
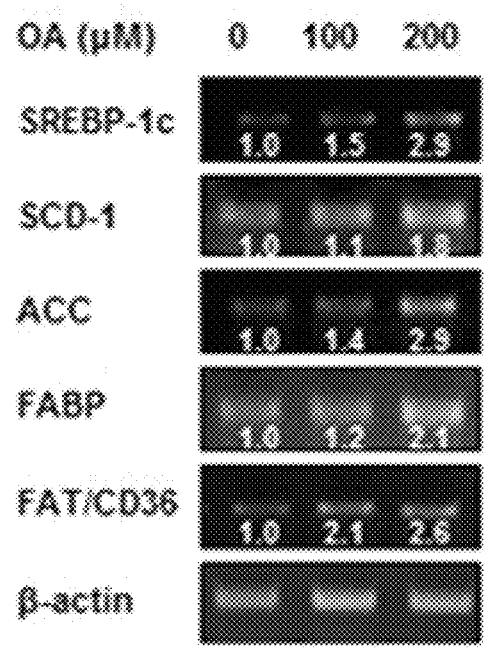
FIG. 6C illustrates verification results of the expression of target genes in HepG2 cells according to oleic acid treatment.
Figure 6D:
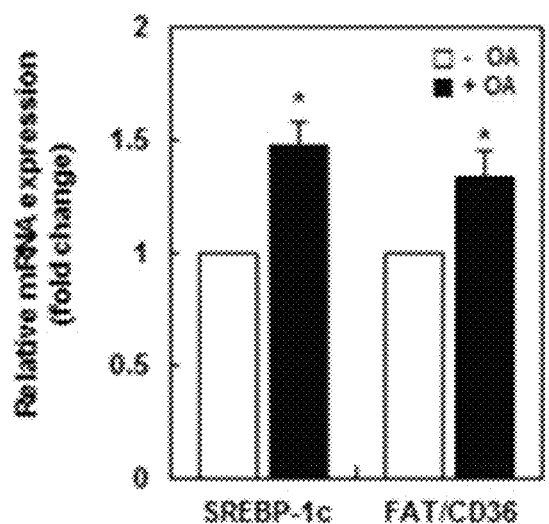
FIG. 6D illustrates verification results of the expression of target genes in primary mouse hepatocytes according to oleic acid treatment.

The mRNA expression of PPARγ$_2$ was increased in an oleic acid concentration-dependent manner. However, there were no changes in mRNA expression amounts of 14-3-3β and 14-3-3γ (see FIGS. 6A and 6B). In addition, the mRNA expression of lipid metabolism-associated genes, which are PPARγ$_2$ target genes, was also increased in an oleic acid concentration-dependent manner (see FIGS. 6C and 6D). As a result of the present experiment, oleic acid increased the expression of PPARγ$_2$ and target genes thereof, and did not affect the expression of 14-3-3β and 14-3-3γ. From the results, it was determined that the regulation of transcriptional activity by binding of 14-3-3β and 14-3-3γ to phosphorylated residues of activated PPARγ$_2$ is more important than the expression of 14-3-3β and 14-3-3γ.

<Example 7> Roles of 14-3-3β and 14-3-3γ in Regulating Expression of Target Gene of PPARγ$_2$ by Oleic Acid HepG2 cells were seeded in a 6-well plate at a density of 4×10$^5$ cells per each well, and then transfected with GFP-14-3-3β DNA (4 μg) or GFP-14-3-3γ DNA (4 μg) using an E-fection plus reagent (Lugen). A ratio of DNA to the E-fection plus reagent was 1:2, and this method was performed according to a manufacturer's manual. After transfection, the cells were treated with 200 μM of oleic acid (OA) for 72 hours, and for mRNA extraction, the corresponding cells were lysed with 1 ml/well of TRIzol (Invitrogen), 200 μl of chloroform was added thereto and mixed well, the resultant cells were maintained at room temperature for 5 minutes and then centrifuged at 12,000×g and 4° C. for 15 minutes, the obtained supernatant was mixed with 500 μl of isopropanol and then put on ice for 10 minutes, and the resulting supernatant was centrifuged at 12,000×g and 4° C. for 15 minutes to remove a supernatant, and then pellets were dissolved with tertiary distilled water treated with diethyl pyrocarbonate (DEPC). 2 μg of mRNA was synthesized into cDNA using a Superscript First Strand cDNA Synthesis Kit (Bioneer, Daejeon, South Korea) and the synthesized cDNA as a template was amplified through polymerase chain reaction (PCR) using primers specific to PPARγ$_2$ (SEQ ID NOS: 1 and 2), 14-3-3β (SEQ ID NOS: 3 and 4), 14-3-3γ (SEQ ID NOS: 5 and 6), SREBP-1c, FAT/CD36, and β-actin of humans, and was amplified through real-time PCR using primers specific to SREBP-1c, FAT/CD36, and GAPDH of mice. β-actin and GAPDH were used as controls to see whether mRNAs of the respective cells were compared in the same amount.

In addition, for chromatin immunoprecipitation (ChIP), HepG2 cells were seeded in a 100 mm plate at a density of 4×10$^6$ cells per each well, and then transfected with Flag-PPARγ$_2$ DNA (4 μg), mGST-14-3-3β DNA (4 μg) or mGST-14-3-3γ DNA (4 μg), and si-14-3-3β (20 μM, Santa Cruz) or si-14-3-3γ (20 μM, Santa Cruz) using an E-fection plus reagent (Lugen). A ratio of DNA to the E-fection plus reagent was 1:2, and this method was performed according to a manufacturer's manual. The corresponding cells were treated with 0.75% formaldehyde at room temperature for 15 minutes, glycine was added thereto, and the resulting cells were scraped into ice-cold PBS and centrifuged at 1,000×g and 4° C. for 3 minutes to remove a supernatant, pellets were dissolved with 400 μl of FA lysis buffer (50 mM HEPES, 150 mM NaCl, 2 mM EDTA pH 8.0, 1% Triton-X100, 0.1% NaDeoxycholate), and then lysed using a sonicator twice for 10 minutes at a high voltage under the following condition: lysis for 30 seconds and resting for 30 seconds. A DNA-protein complex was immunoprecipitated using an anti-Flag antibody (Santa Cruz), and then amplified through PCR using FAT/CD36 promoter-specific primers.

In addition, HepG2 cells were seeded in a 6-well plate at a density of 5×10$^5$ cells per each well, and then transfected with HA-14-3-3β DNA (1 μg) or HA-14-3-3γ DNA (1 μg) using an E-fection plus reagent (Lugen). A ratio of DNA to the E-fection plus reagent was 1:2, and this method was performed according to a manufacturer's manual. After transfection, the cells were treated with 200 μM of oleic acid (OA) for 72 hours, washed with ice-cold PBS, and lysed with 80 μl/well of a lysis buffer (150 mM NaCl, 1 mM EDTA, 1% Nonidet P-40, 5% glycerol, 25 mM tris-HCl, pH 7.5, protease inhibitor added), the lysed cells were centrifuged at 10,000×g and 4° C. for 10 minutes to extract proteins, and 30 μg of the proteins was separated on a 10% SDS-PAGE gel and identified using each of the antibodies (HA, SREBP-1c: Santa Cruz) by western blotting, and all antibodies were used in a ratio of 1:3000.

Figure 7A:
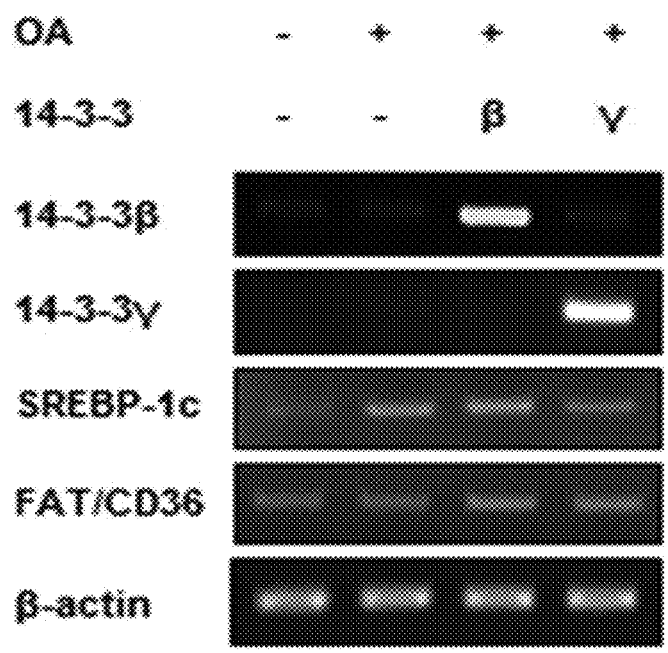
FIG. 7A illustrates verification results of the expression of target genes according to the expression of 14-3-3β and 14-3-3γ in HepG2 cells.
Figure 7B:
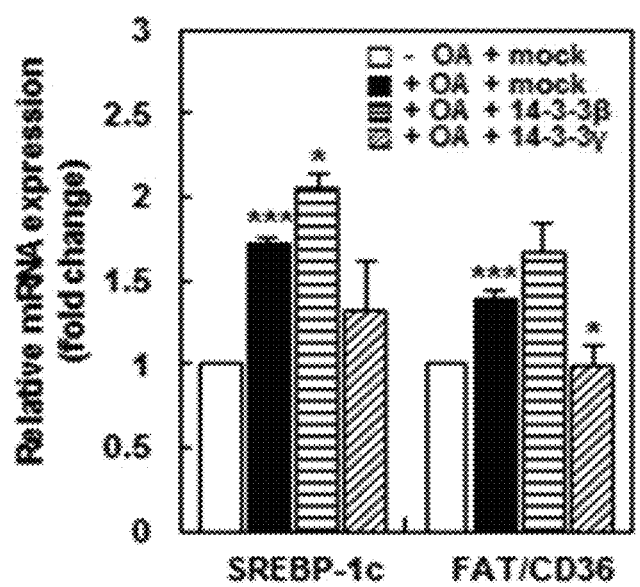
FIG. 7B illustrates verification results of the expression of target genes according to the expression of 14-3-3β and 14-3-3γ in primary mouse hepatocytes.

The mRNA expression of sterol regulatory element binding protein-1c (SREBP-1c) and fatty acid translocase (FAT)/CD36, increased by oleic acid, was further increased by overexpression of 14-3-3β. However, when 14-3-3γ was overexpressed, the expression of mRNA of SREBP-1c and FAT/CD36 was reduced (see FIGS. 7A and 7B).

In addition, the binding of PPARγ$_2$ and a binding strength thereof according to the expression of 14-3-3β and 14-3-3γ were evaluated by ChIP assay using a PPAR response element (PPRE) known as a binding site of PPARγ$_2$ present in the FAT/CD36 promoter. As a result, the binding of PPARγ$_2$ to the FAT/CD36 promoter was increased during the overexpression of 14-3-3β, and inhibited during the overexpression of 14-3-3γ (see FIG. 7C, upper side).

Figure 7C:
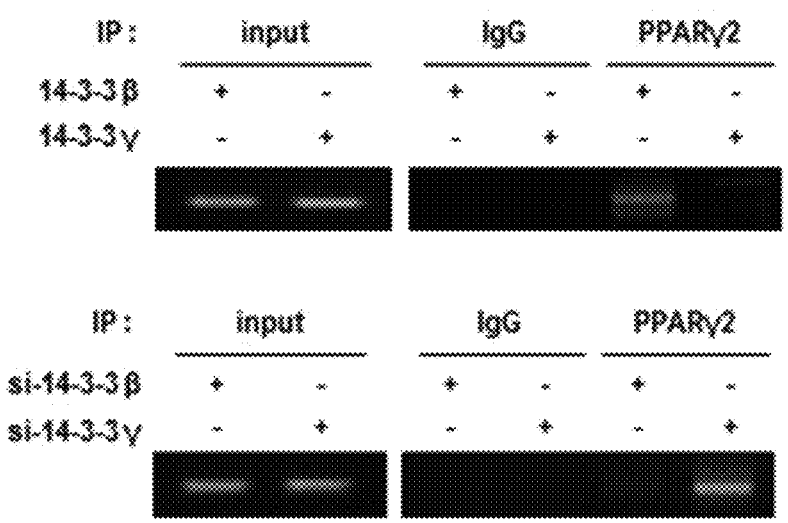
FIG. 7C illustrates verification results of binding with a FAT/CD36 promoter according to the expression of 14-3-3β and 14-3-3γ by chromatin immunoprecipitation (ChIP assay).

However, it was seen that, when the expression of 14-3-3β was inhibited, the binding strength between PPARγ$_2$ and 14-3-3β was poor, and, when the expression of 14-3-3γ was inhibited, the binding strength therebetween was increased (see FIG. 7C, lower side).

These results indicate that PPARγ$_2$, which binds to a promoter region to regulate the expression of the CD36 gene, is increased by 14-3-3β and reduced by 14-3-3γ.

Figure 7D:
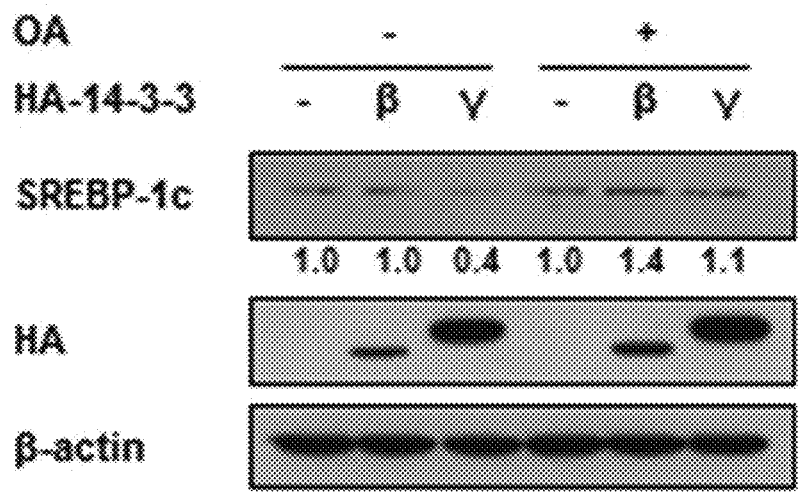
FIG. 7D illustrates verification results of the expression of the SREBP-1c protein according to the expression of 14-3-3β and 14-3-3γ.

To verify whether such regulation of mRNA expression of the target genes of PPARγ$_2$ is the same as in the expression of a protein thereof, an expression amount of the SREBP-1c protein was checked by western blotting. As a result of the experiment, it was confirmed that the expression of the SREBP-1c protein was increased by the overexpression of 14-3-3β and reduced by the overexpression of 14-3-3γ (see FIG. 7D).

Thus, from the above experimental results, it was confirmed that the expression and activation of PPARγ$_2$ were increased by fatty acid stimulation, and an increased transcriptional activity of PPARγ$_2$ was regulated by 14-3-3β and 14-3-3γ in opposite ways.

<Example 8> Binding of PPARγ$_2$ to 14-3-3β and 14-3-3γ According to Activation of PPARγ$_2$ HEK-293T cells were seeded in a 100 mm plate at a density of 2×10$^6$ cells per each well, and then transfected with mGST-PPARγ$_2$ DNA (4 μg) and HA-14-3-3β DNA (4 μg) or HA-14-3-3γ DNA (4 μg) using an E-fection plus reagent (Lugen). A ratio of DNA to the E-fection plus reagent was 1:2, and this method was performed according to a manufacturer's manual. After transfection, the cells were treated with 200 μM of oleic acid (OA) for 72 hours, washed with ice-cold PBS, and lysed with 500 μl/well of a lysis buffer (150 mM NaCl, 1 mM EDTA, 1% Nonidet P-40, 5% glycerol, 25 mM tris-HCl, pH 7.5, protease inhibitor added), the lysed cells were centrifuged at 10,000×g and 4° C. for 10 minutes to extract proteins, 1,000 μg of the proteins was reacted with 20 μl of glutathione Sepharose 4B beads (GE Healthcare, Buckinghamshire, UK) for 6 hours, washing of the beads with 1 ml of ice-cold PBS was repeated 5 times, the resulting beads were boiled at 100° C. for 10 minutes, and the proteins were separated on a 10% SDS-PAGE gel and identified using each of the antibodies (GST, HA: Santa Cruz) by western blotting, and all antibodies were used in a ratio of 1:3000.

Figure 8A:
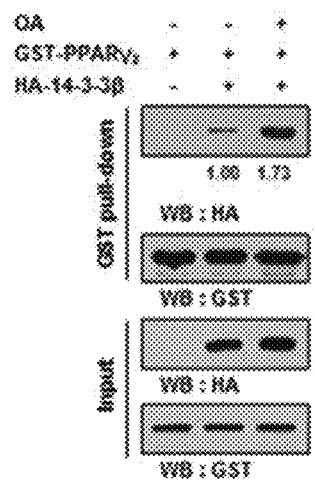
Figure 8B:
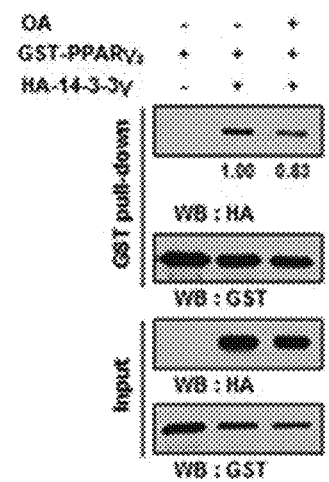
Figure 8C:
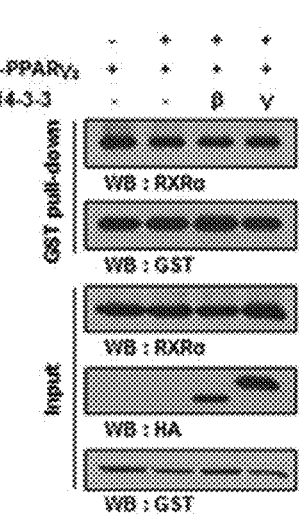

When oleic acid was treated, binding between PPARγ$_2$ and 14-3-3β was increased (see FIG. 8A), but binding between PPARγ$_2$ and 14-3-3γ was reduced (see FIG. 8B). According to reports known to date, a PPAR-RXR complex is known to play a vital role in metabolic regulation and metabolism-associated gene expression. Thus, as a result of seeing whether the overexpression of 14-3-3β and 14-3-3γ affects formation of the PPAR-RXR complex, it was confirmed that it did not affect the formation of the PPAR-RXR complex (see FIG. 8C). That is, PPARγ$_2$ having an increased activity due to oleic acid had increased binding with 14-3-3β and decreased binding with 14-3-3γ, and was not involved in the formation of a PPARγ$_2$-RXRα complex.

<Example 9> Roles of 14-3-3β and 14-3-3γ in Hepatocyte Lipid Accumulation by Oleic Acid Treatment HepG2 cells and primary mouse hepatocytes were separately seeded in a 6-well plate at a density of 4×10$^5$ cells per each well, and then transfected with GFP-14-3-3β DNA (1 μg) or GFP-14-3-3γ DNA (1 μg) and si-14-3-3β (10 μM, Santa Cruz) or si-14-3-3γ (10 μM, Santa Cruz) using an E-fection plus reagent (Lugen). A ratio of DNA to the E-fection plus reagent was 1:2, and this method was performed according to a manufacturer's manual. After transfection, the cells were treated with 200 μM of oleic acid (OA) for 72 hours, washed with ice-cold PBS, fixed with 4% paraformaldehyde, and then stained with a 0.35% Oil Red-O solution at room temperature for 6 hours. The stained cells were bleached with 1 ml of isopropanol and analyzed at a wavelength of 550 nm using a DU530 spectrophotometer (Beckman Instruments, Palo Alto, Calif.).

Figure 9A:
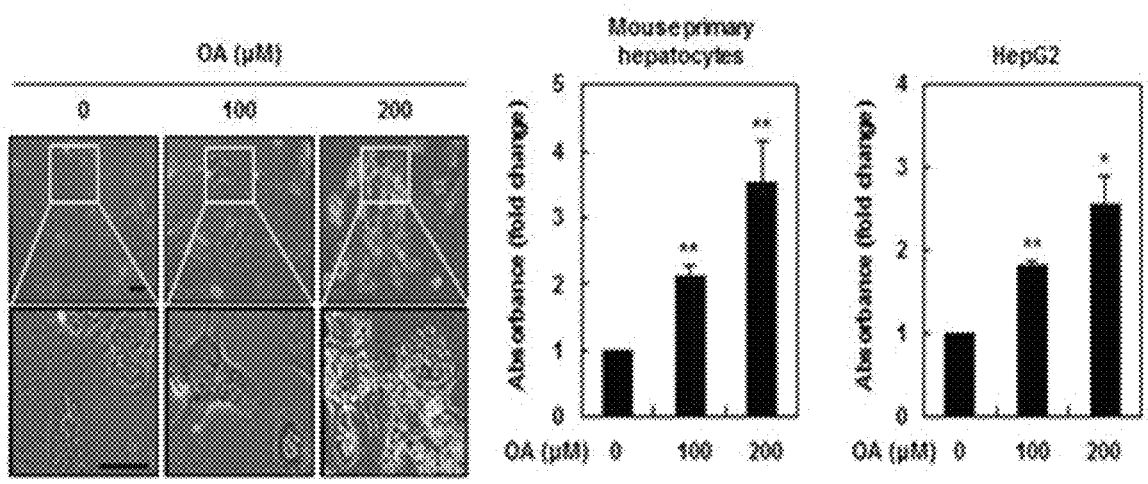
Figure 9B:
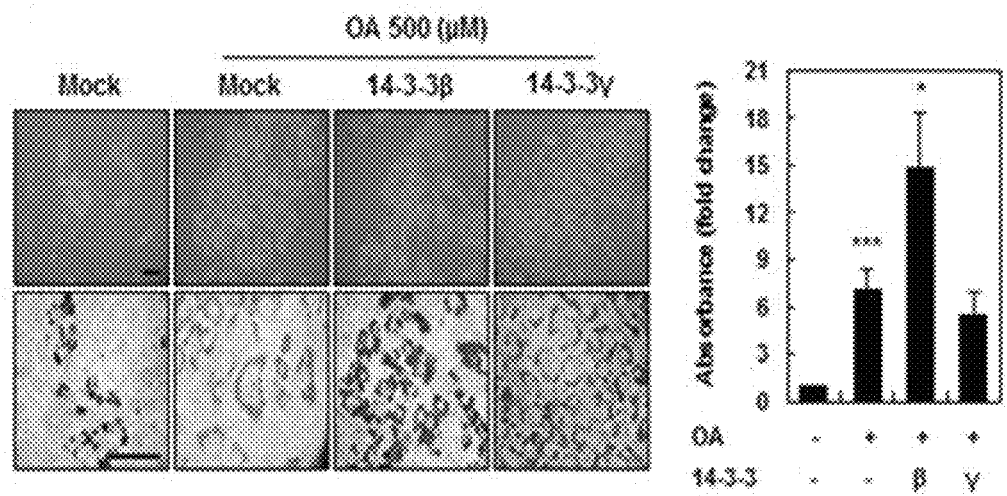
Figure 9C:
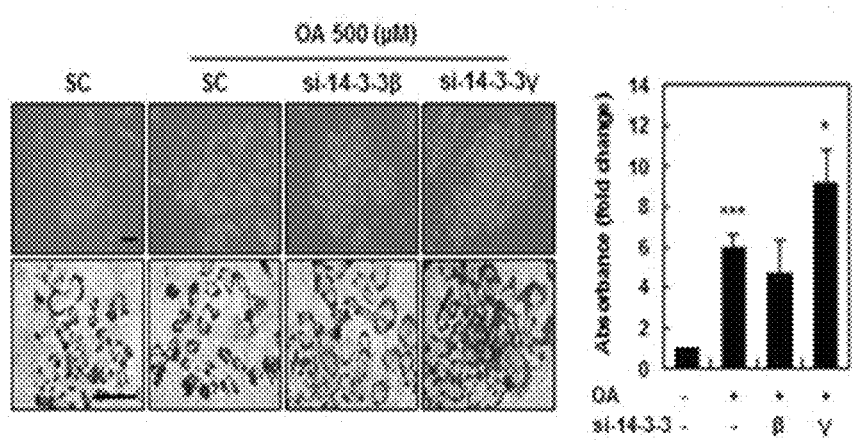

As a result of the concentration-dependent treatment of oleic acid, lipid accumulation was increased in the primary mouse hepatocytes and the HepG2 cells (see FIG. 9A). The overexpression of 14-3-3β increased lipid accumulation by oleic acid, and the overexpression of 14-3-3γ reduced lipid accumulation (see FIG. 9B). In addition, when the expression of 14-3-3β was inhibited via si-14-3-3β, lipid accumulation was reduced, and, when the expression of 14-3-3γ was inhibited, lipid accumulation was increased (see FIG. 9C).

These experimental results demonstrate that the activity of PPARγ$_2$ that had been increased by oleic acid was further increased by 14-3-3β, resulting in increased lipid accumulation, and the activity of PPARγ$_2$ was reduced by 14-3-3γ, resulting in reduced lipid accumulation.

<Example 10> Roles of 14-3-3β and 14-3-3γ in Triglyceride Accumulation

A triglyceride (neutral fat) is a type of fatty acid and is used as an index of a fat content. A biochemical lipid test was carried out by measuring an amount of triglycerides.

HepG2 cells and primary mouse hepatocytes were separately seeded in a 6-well plate at a density of 4×10$^5$ cells per each well, and then transfected with GFP-14-3-3β DNA (1 μg) or GFP-14-3-3γ DNA (1 μg) and si-14-3-3β (10 μM, Santa Cruz) or si-14-3-3γ (10 μM, Santa Cruz) using an E-fection plus reagent (Lugen). A ratio of DNA to the E-fection plus reagent was 1:2, and this method was performed according to a manufacturer's manual. After transfection, the cells were treated with 200 μM of oleic acid (OA) for 72 hours, and the amount of triglycerides was measured using a triglyceride colorimetric assay kit (Cayman Chemical). The corresponding cells were washed with ice-cold PBS and then scraped using a standard diluent assay reagent, the scrapping process was repeated using a sonicator 20 times to lyse the cells, and the lysed cells were reacted with an enzyme buffer solution for 15 minutes, followed by measurement using an ELISA reader (Bio-Rad Laboratories, Inc) at a wavelength of 550 nm.

Figure 10A:
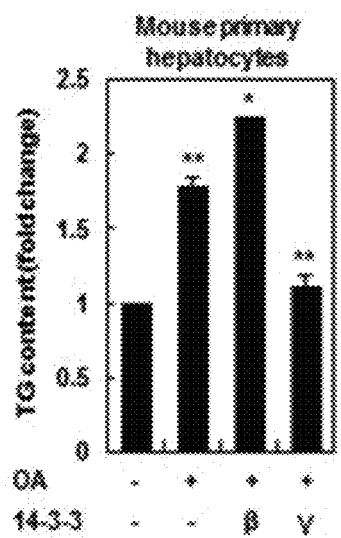
Figure 10B:
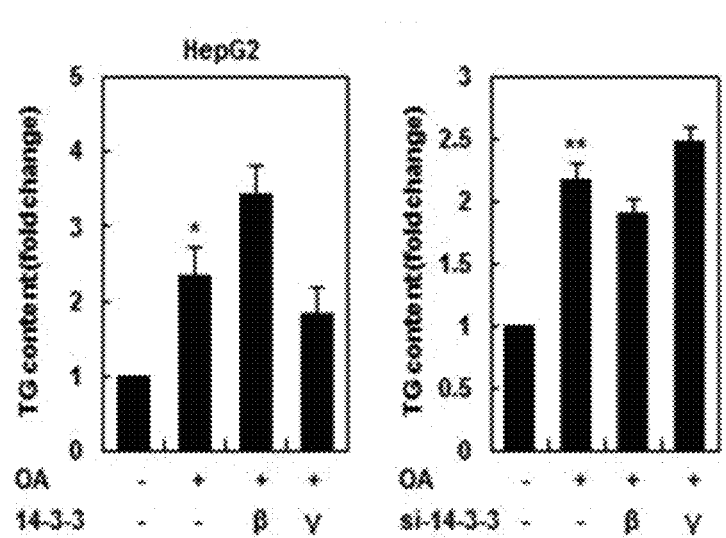

As in the lipid accumulation results, triglyceride accumulation was increased when the primary mouse hepatocytes were treated with oleic acid, triglyceride accumulation was further increased according to the overexpression of 14-3-3β, and the overexpression of 14-3-3γ reduced triglyceride accumulation (see FIG. 10A). In addition, the inhibition of 14-3-3β expression reduced triglyceride accumulation, and the inhibition of 14-3-3γ expression increased triglyceride accumulation (see FIG. 10B).

Taking all the above results into consideration, it can be confirmed that 14-3-3β and 14-3-3γ bind to the same residue of PPARγ$_2$ to regulate the activity of PPARγ$_2$ in opposite manners, and competitively perform regulation thereof. Under basal conditions, basal metabolism is maintained such that binding of 14-3-3β and 14-3-3γ to the S273 residue of PPARγ$_2$ is balanced, and under a highly concentrated fatty acid condition, binding of 14-3-3β to the S273 residue of PPARγ$_2$ is increased, which leads to increased lipid accumulation, and, accordingly, it is expected to develop into non-alcoholic fatty liver. Therefore, non-alcoholic fatty liver is expected to be prevented or treated by regulating the activity of PPARγ$_2$ through the regulation of expression amounts of 14-3-3β and 14-3-3γ.

What is claimed is:

1. A method of screening a drug for treating a non-alcoholic fatty liver and treating the non-alcoholic fatty liver, the method comprising:
    a contacting step of contacting 14-3-3β proteins into contact with a candidate material together with the PPARγ2 proteins in vitro;
    a measuring step of measuring a change in binding of the 14-3-3β proteins to the PPARγ2 proteins by the candidate material, wherein when the candidate material down-regulates the binding of the 14-3-3β proteins to the PPARγ2 proteins, the candidate material is selected as a screened drug having an effect on treating the non-alcoholic fatty liver; and
    an administering step of administering an effective amount of the screened drug, which down-regulates the binding of the 14-3-3β proteins to the PPARγ2 proteins and thus having the effect on treating the non-alcoholic fatty liver, to a subject in need thereof.

2. The method of claim 1, wherein the measuring step is performed by measuring a change in binding of the 14-3-3β proteins to the Ser273 residue of PPARγ2.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: PPAR gamma2 forward

<400> SEQUENCE: 1
atgggtgaaa ctctgggaga                                             20

<210> SEQ ID NO 2
<211> LENGTH: 20
<212> TYPE: DNA
<213> ORGANISM: Artificial Sequence
<220> FEATURE:
<223> OTHER INFORMATION: PPAR gamma2 reverse
```

```
<400> SEQUENCE: 2
gggcttgatg tcaaaggaat                                               20

<210> SEQ ID NO 3
<211> LENGTH: 20
<212> TYPE: DNA
<213> ORGANISM: Artificial Sequence
<220> FEATURE:
<223> OTHER INFORMATION: 14-3-3beta forward

<400> SEQUENCE: 3
aaagagtacc gtgagaagat                                               20

<210> SEQ ID NO 4
<211> LENGTH: 20
<212> TYPE: DNA
<213> ORGANISM: Artificial Sequence
<220> FEATURE:
<223> OTHER INFORMATION: 14-3-3beta reverse

<400> SEQUENCE: 4
ggacaccgtg gtttgtttat                                               20

<210> SEQ ID NO 5
<211> LENGTH: 19
<212> TYPE: DNA
<213> ORGANISM: Artificial Sequence
<220> FEATURE:
<223> OTHER INFORMATION: 14-3-3gamma forward

<400> SEQUENCE: 5
agcgagaccc agtacgaga                                                19

<210> SEQ ID NO 6
<211> LENGTH: 20
<212> TYPE: DNA
<213> ORGANISM: Artificial Sequence
<220> FEATURE:
<223> OTHER INFORMATION: 14-3-3gamma reverse

<400> SEQUENCE: 6
tgcatgtgct ccttgctgat                                               20
```